US005720763A

United States Patent [19]
Tovey

[11] Patent Number: 5,720,763
[45] Date of Patent: Feb. 24, 1998

[54] SURGICAL INSTRUMENT FOR EXPANDING BODY TISSUE

[75] Inventor: H. Jonathan Tovey, Milford, Conn.

[73] Assignee: United States Surgical Corporation, Norwalk, Conn.

[21] Appl. No.: 434,965

[22] Filed: May 4, 1995

Related U.S. Application Data

[62] Division of Ser. No. 124,778, Sep. 21, 1993, abandoned.

[51] Int. Cl.$^6$ ................................................. A61B 17/00
[52] U.S. Cl. ............................................. 606/198; 604/104
[58] Field of Search ........................... 606/108, 1, 191, 606/198; 128/899; 604/53, 104–109; 600/201, 203, 206, 214, 215

[56] References Cited

U.S. PATENT DOCUMENTS

| 769,829 | 9/1904 | Mott . |
| 1,607,194 | 11/1926 | Gammon et al. . |
| 2,184,642 | 12/1939 | Glass . |
| 2,541,246 | 2/1951 | Held . |
| 3,495,586 | 2/1970 | Regenbogen . |
| 3,557,794 | 1/1971 | Van Patten . |
| 3,902,498 | 9/1975 | Niederer . |
| 3,995,619 | 12/1976 | Glatzer . |
| 4,168,709 | 9/1979 | Banton . |
| 4,190,042 | 2/1980 | Sinnreich . |
| 4,585,000 | 4/1986 | Harshenson . |
| 4,620,547 | 11/1986 | Boebel . |
| 4,744,363 | 5/1988 | Hasson . |
| 4,942,869 | 7/1990 | Borodulin et al. . |
| 4,962,770 | 10/1990 | Agee et al. . |
| 4,963,147 | 10/1990 | Agee et al. . |
| 5,029,573 | 7/1991 | Chow . |
| 5,089,000 | 2/1992 | Agee et al. . |
| 5,176,695 | 1/1993 | Dulebohn . |
| 5,178,133 | 1/1993 | Pena . |
| 5,179,963 | 1/1993 | Berger . |
| 5,183,464 | 2/1993 | Dubrul et al. . |
| 5,195,507 | 3/1993 | Bilweis . |
| 5,197,971 | 3/1993 | Bonutti . |
| 5,199,419 | 4/1993 | Remiszewski et al. . |
| 5,235,966 | 8/1993 | Jamner . |
| 5,273,024 | 12/1993 | Menon et al. . |
| 5,358,496 | 10/1994 | Ortiz et al. ........................ 606/198 |

FOREIGN PATENT DOCUMENTS

| 369320 | of 0000 | Germany . |
| WO8910093 | 2/1989 | WIPO . |
| WO9101773 | 7/1990 | WIPO . |
| 92/20399 | 11/1992 | WIPO . |

Primary Examiner—William Lewis

[57] ABSTRACT

A surgical instrument for performing procedures such as carpal tunnel release. The instrument consists of an elongated member having a spring or cam plate positioned therein. The spring or cam plate is movable from a retracted position within the elongated member to an extended position protruding through an aperture in the elongated member. Movement of the spring or cam plate to the extended position stretches a flexible membrane positioned over at least a portion of the elongated member to stretch the carpal tunnel ligament.

17 Claims, 21 Drawing Sheets

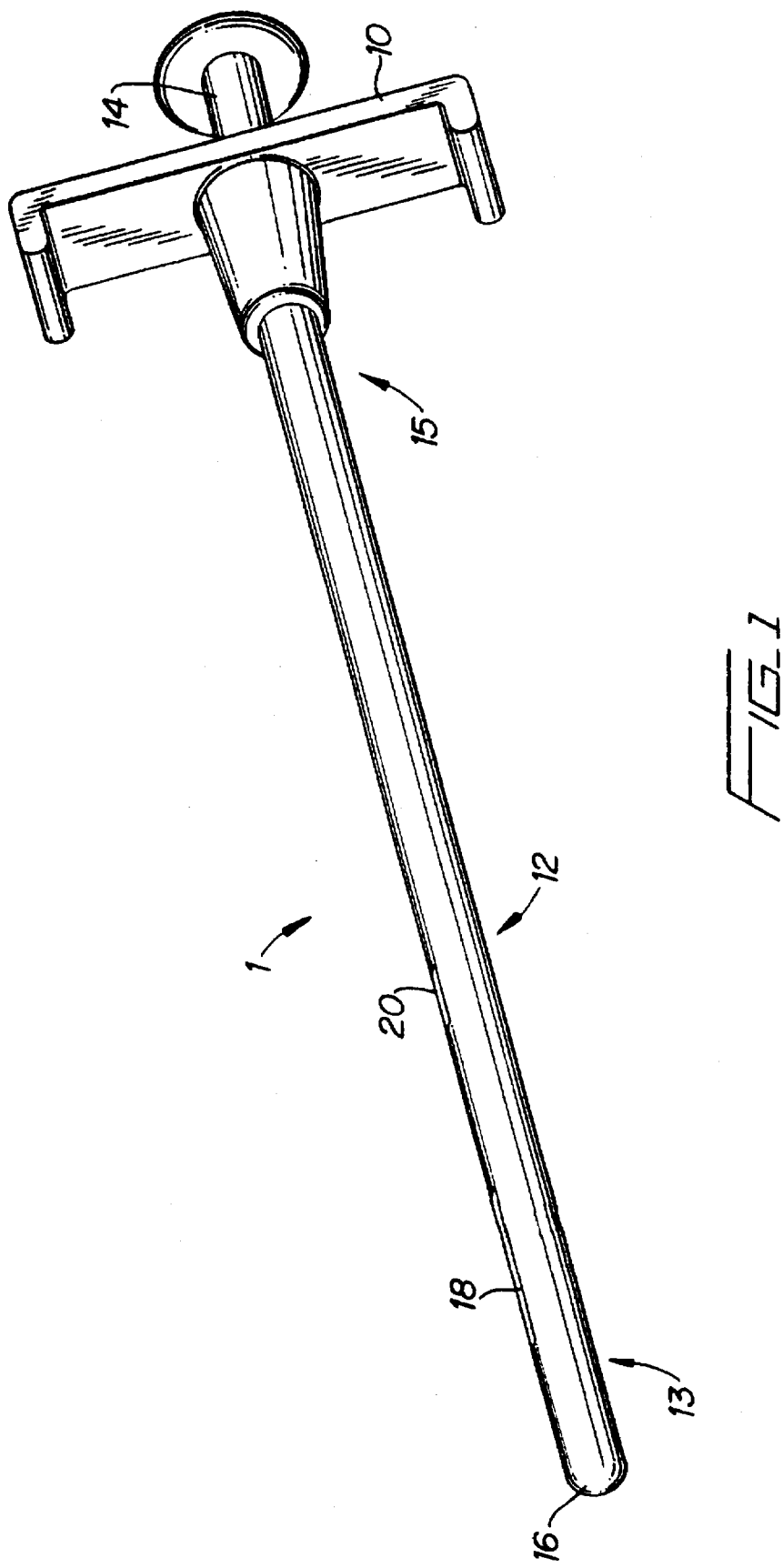

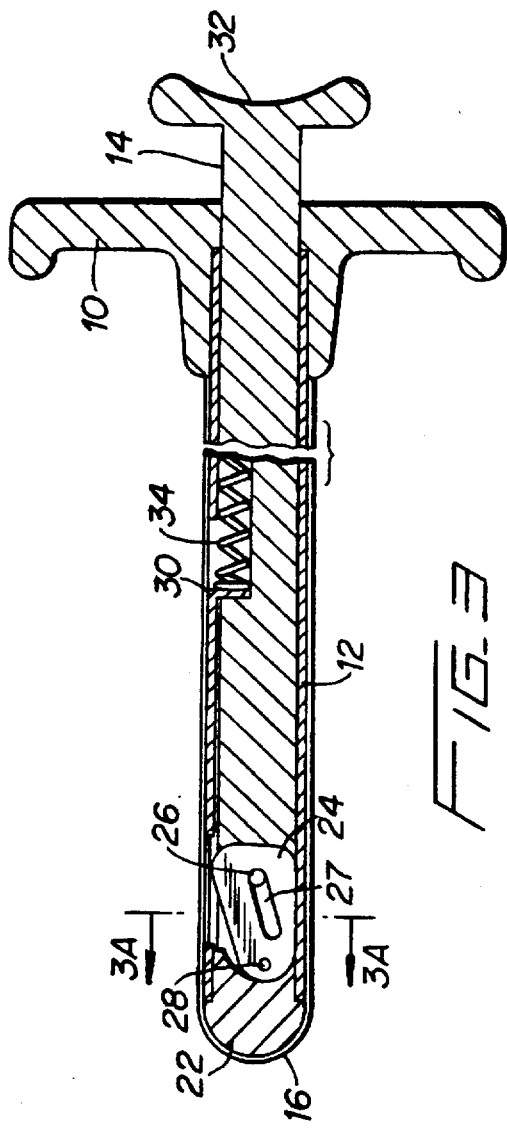
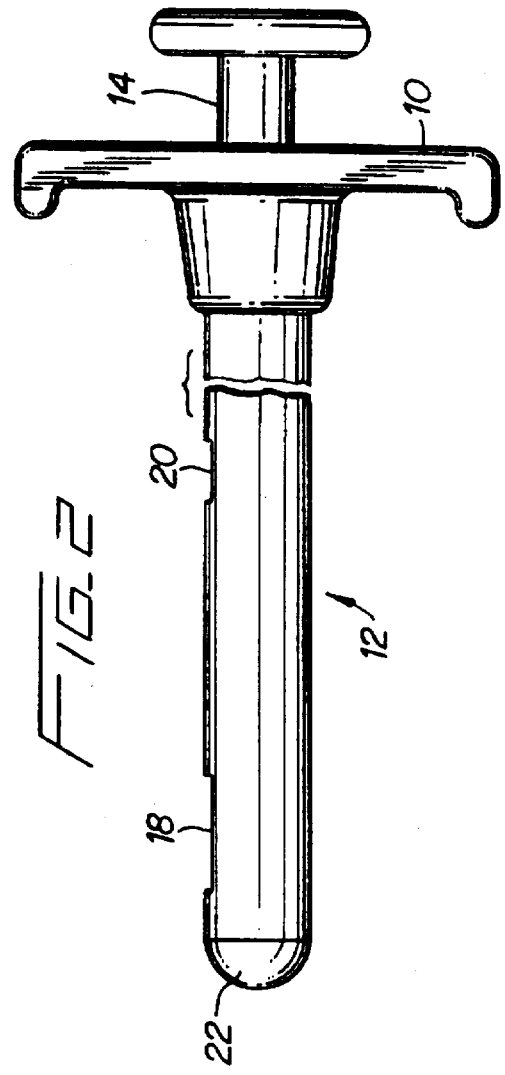
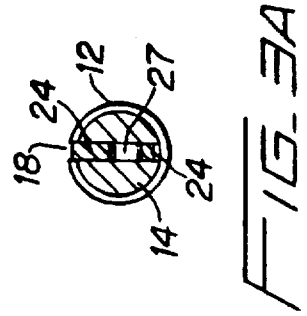

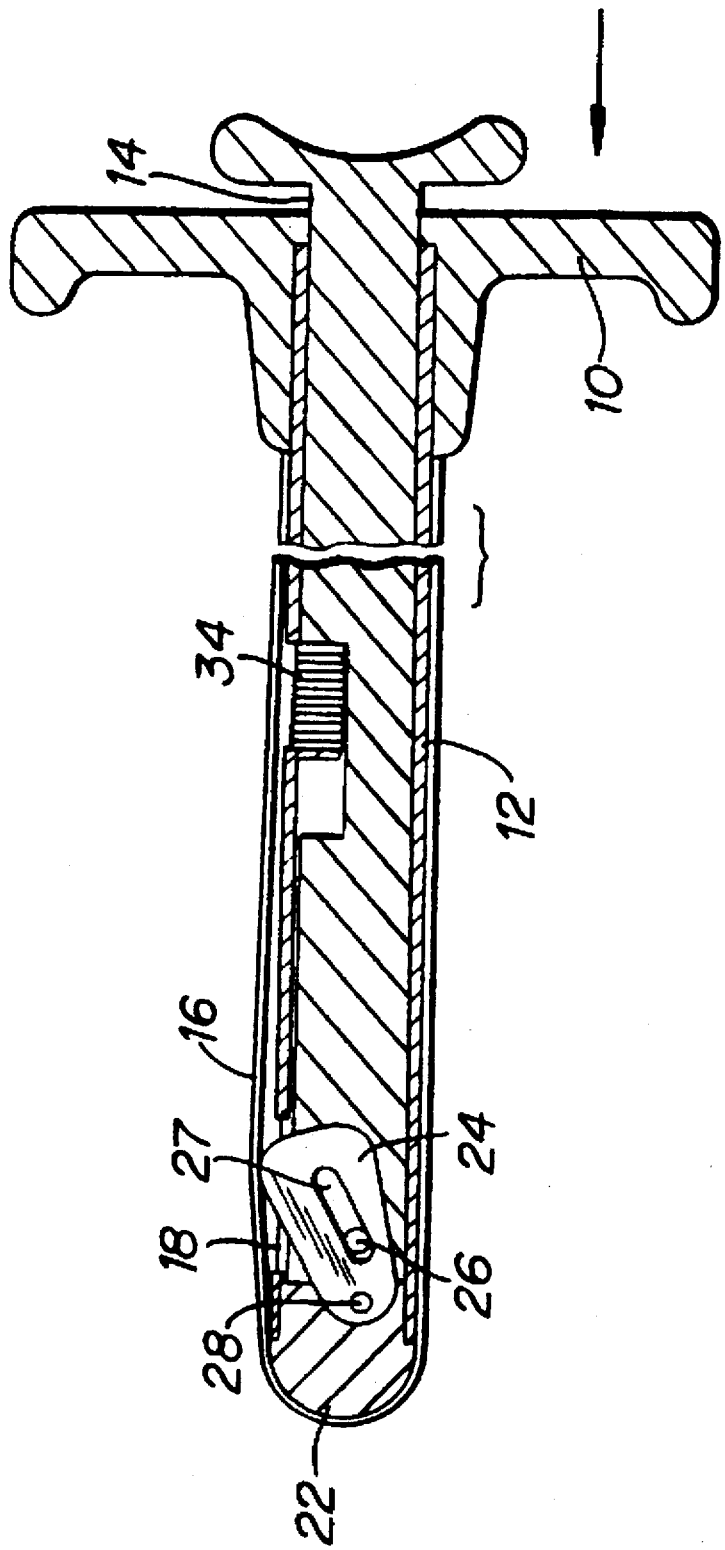

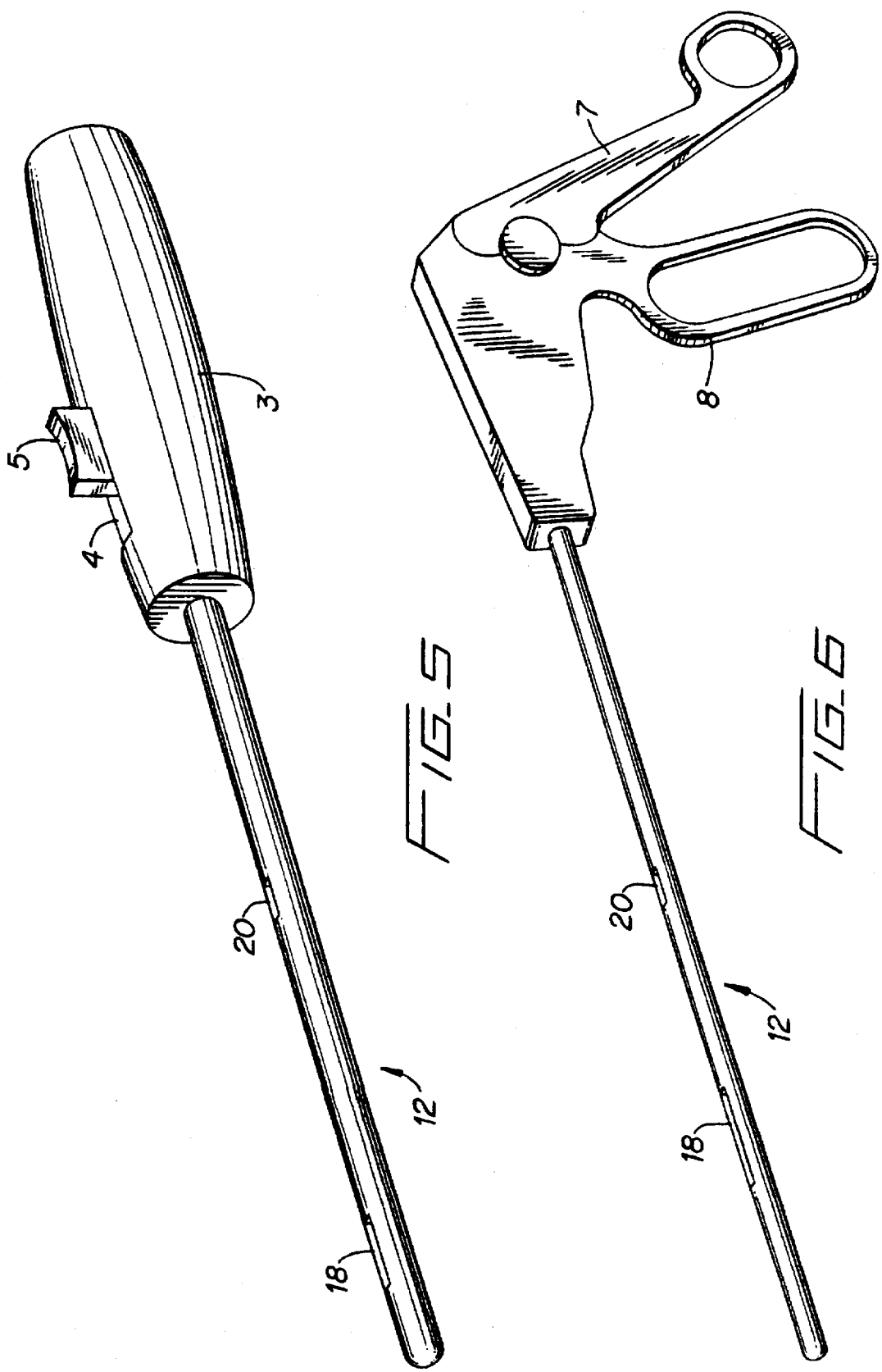

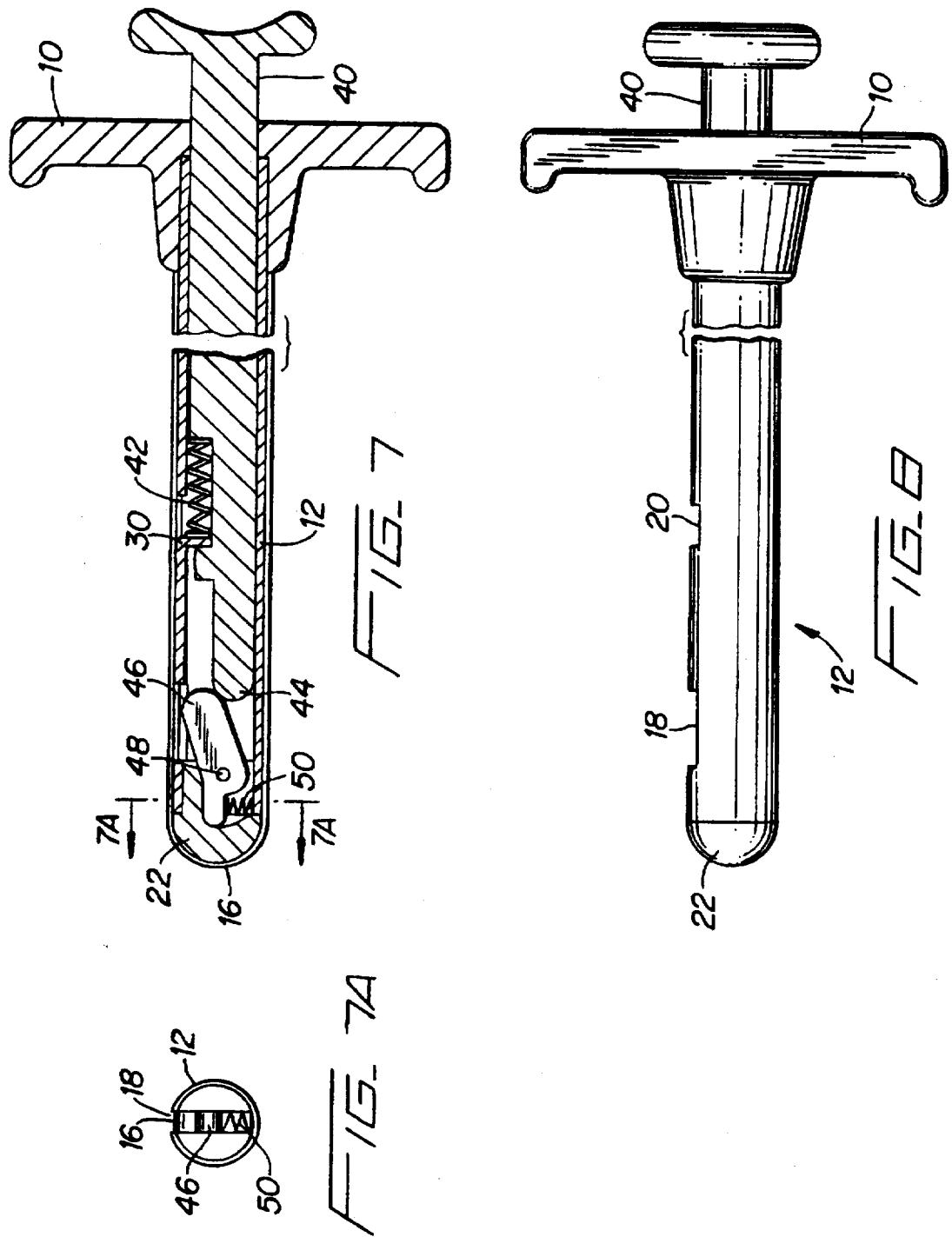

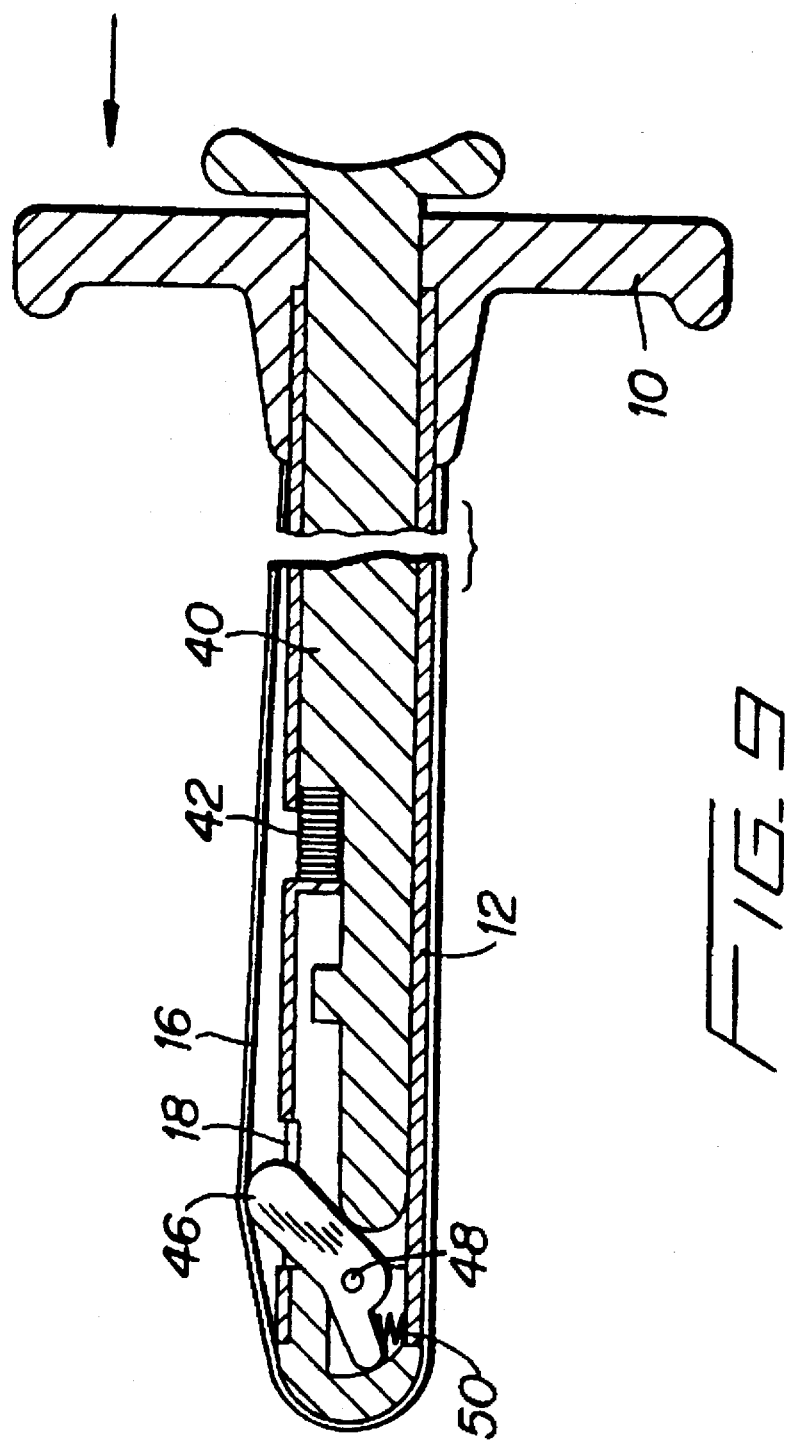

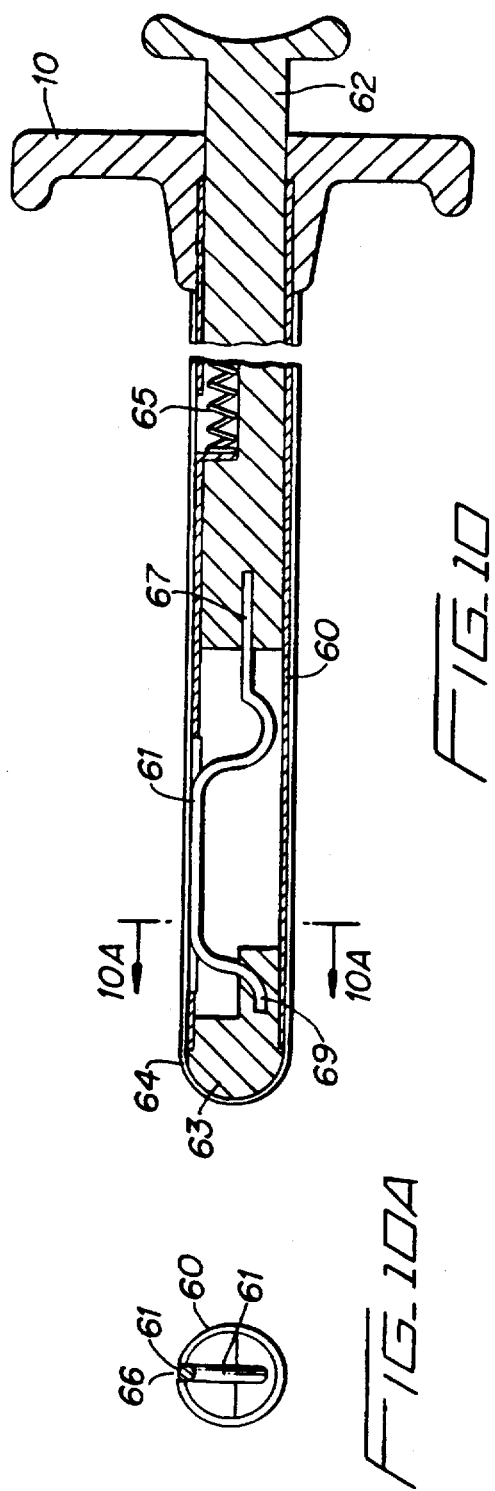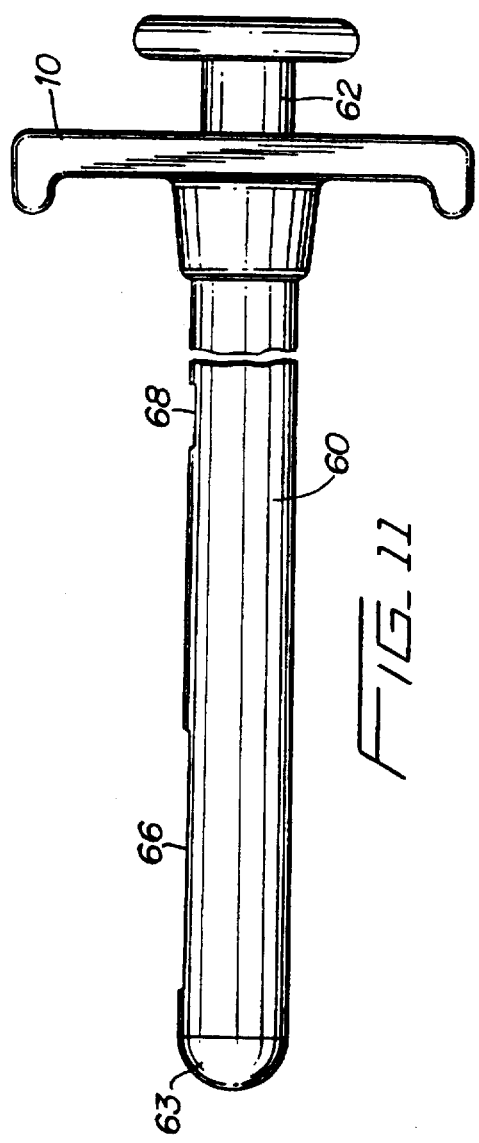
FIG. 10
FIG. 10A
FIG. 11

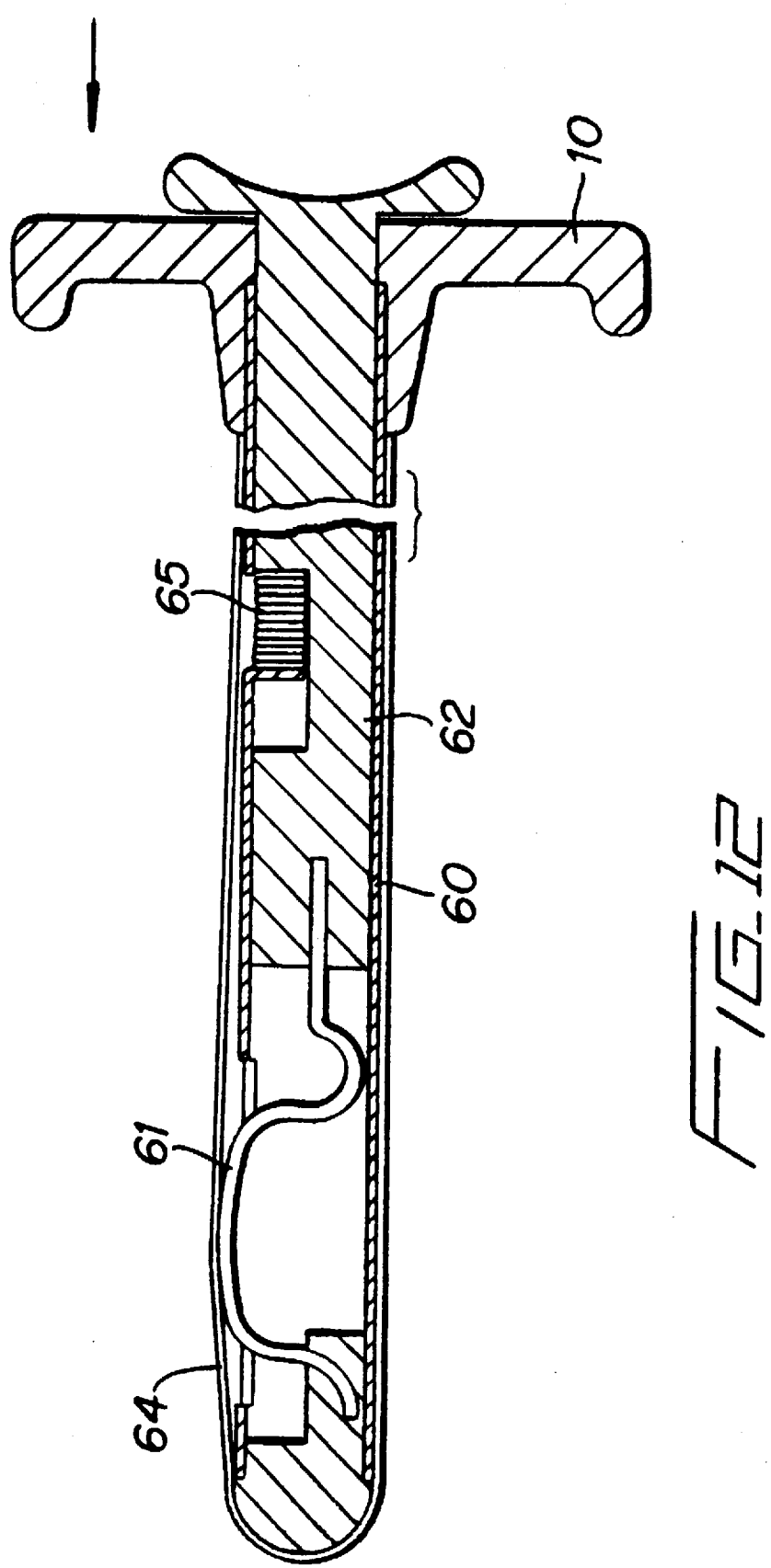

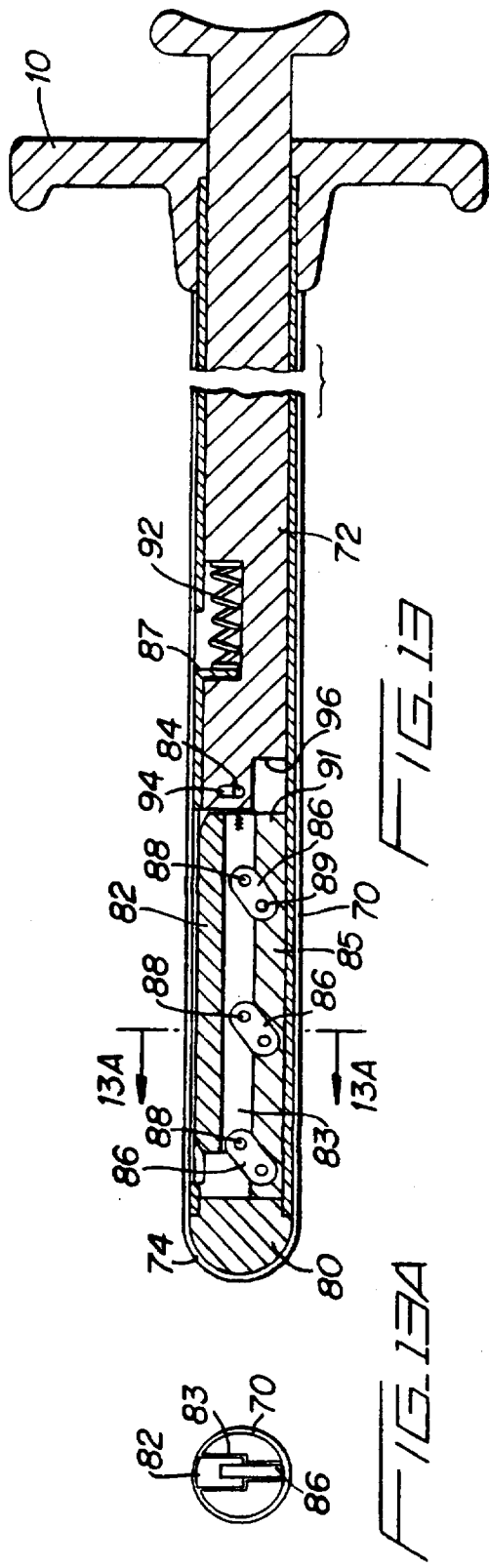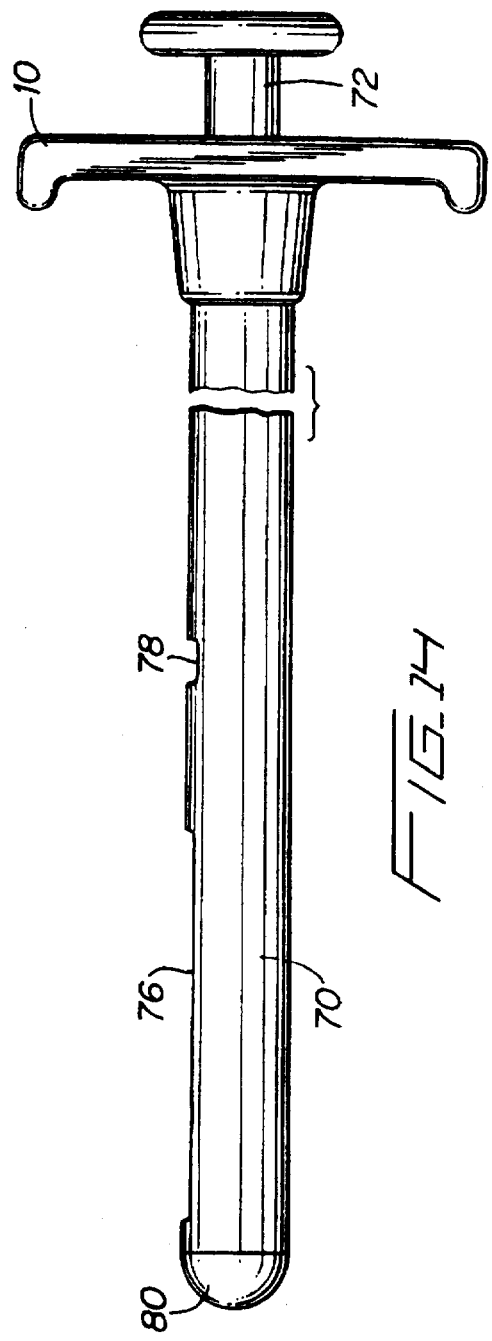

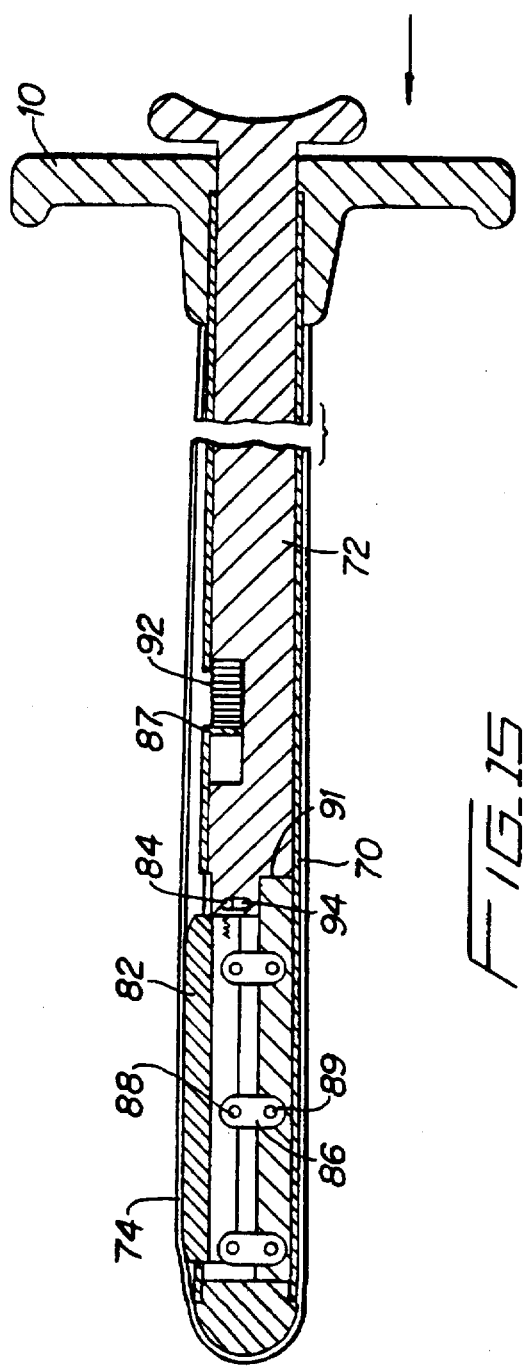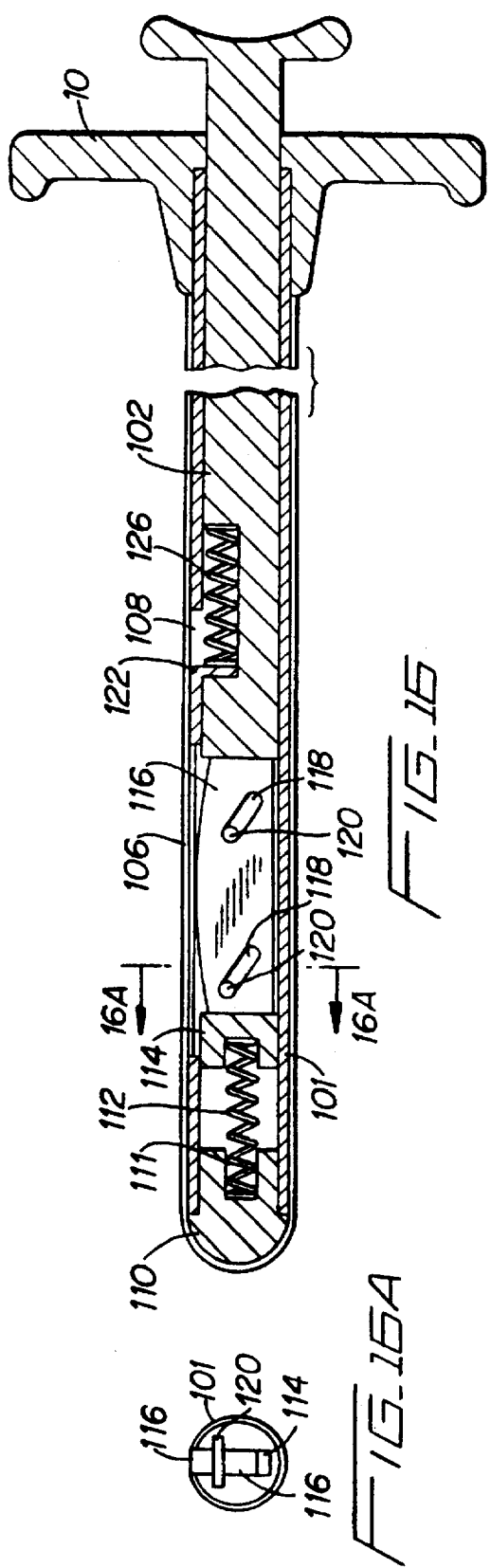

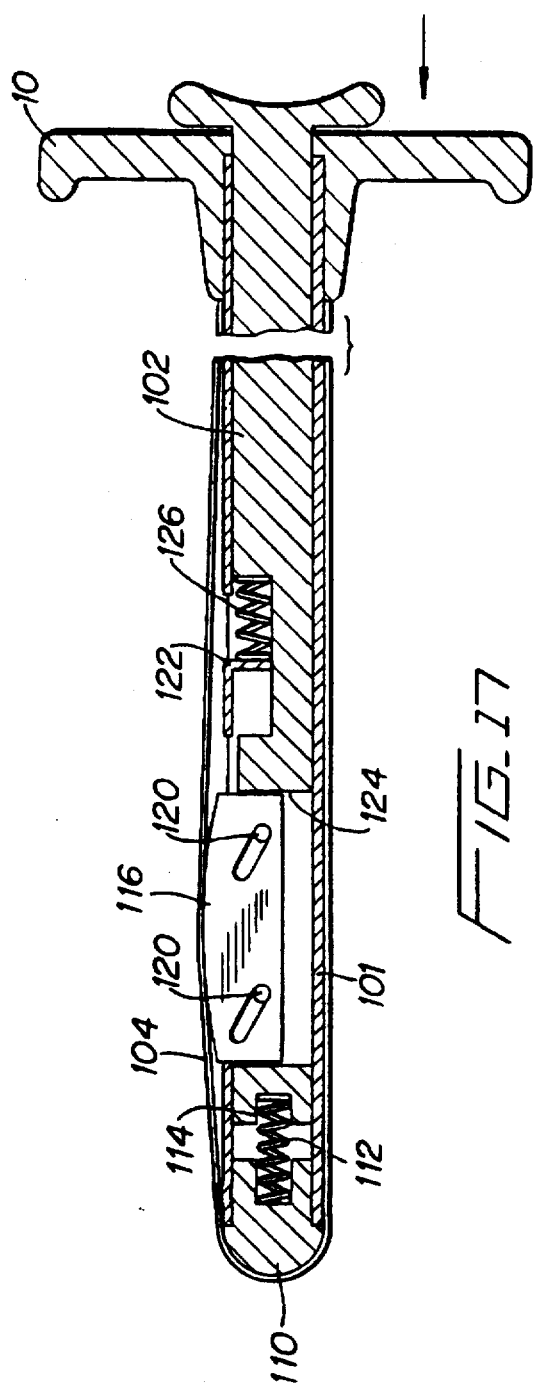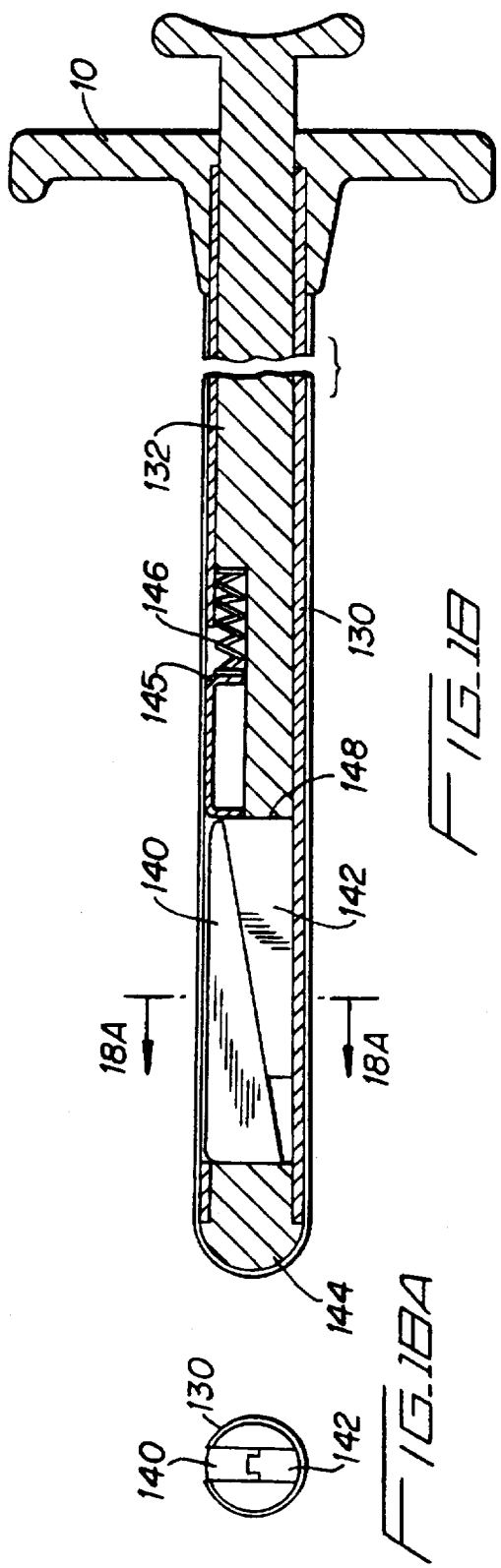

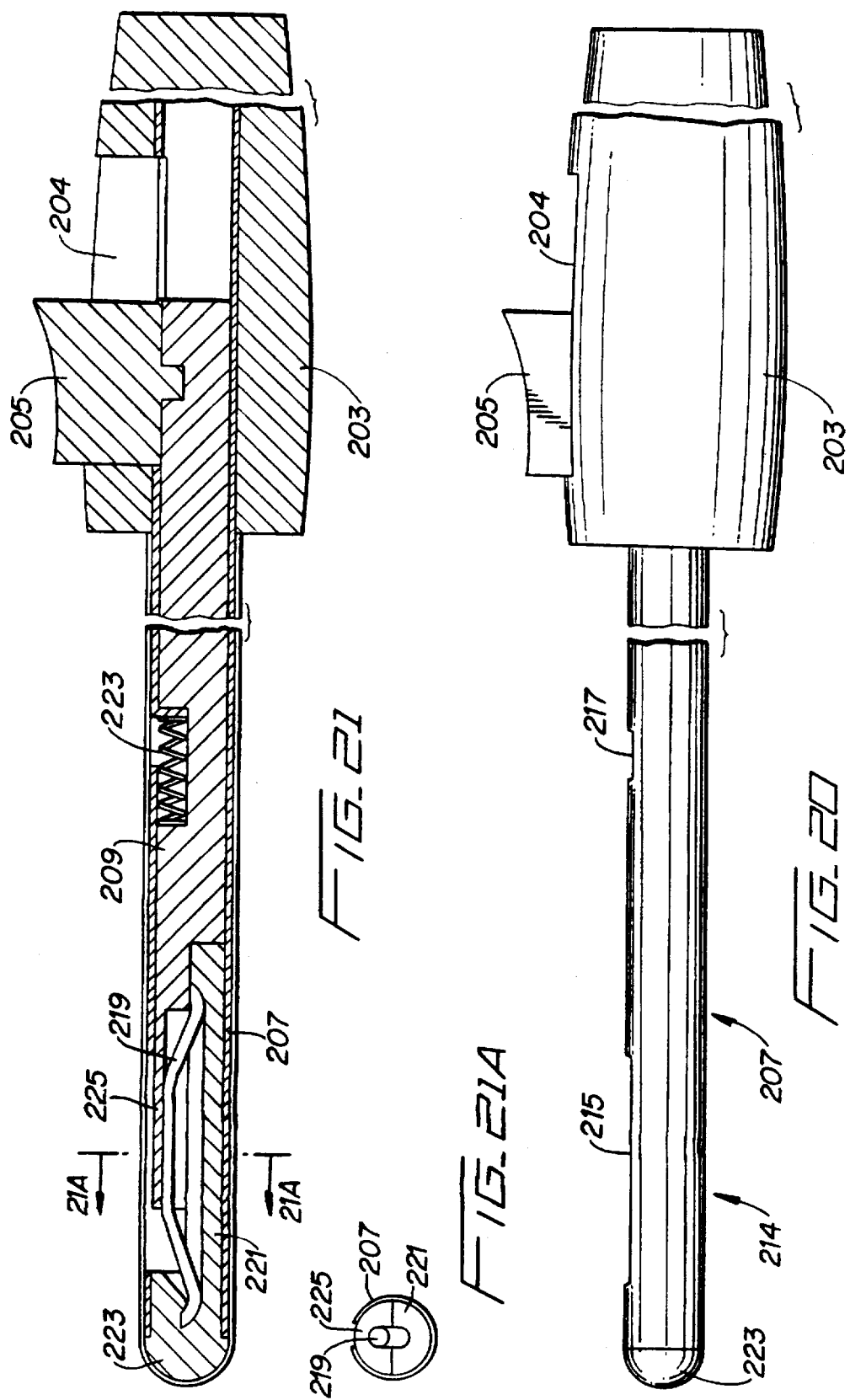

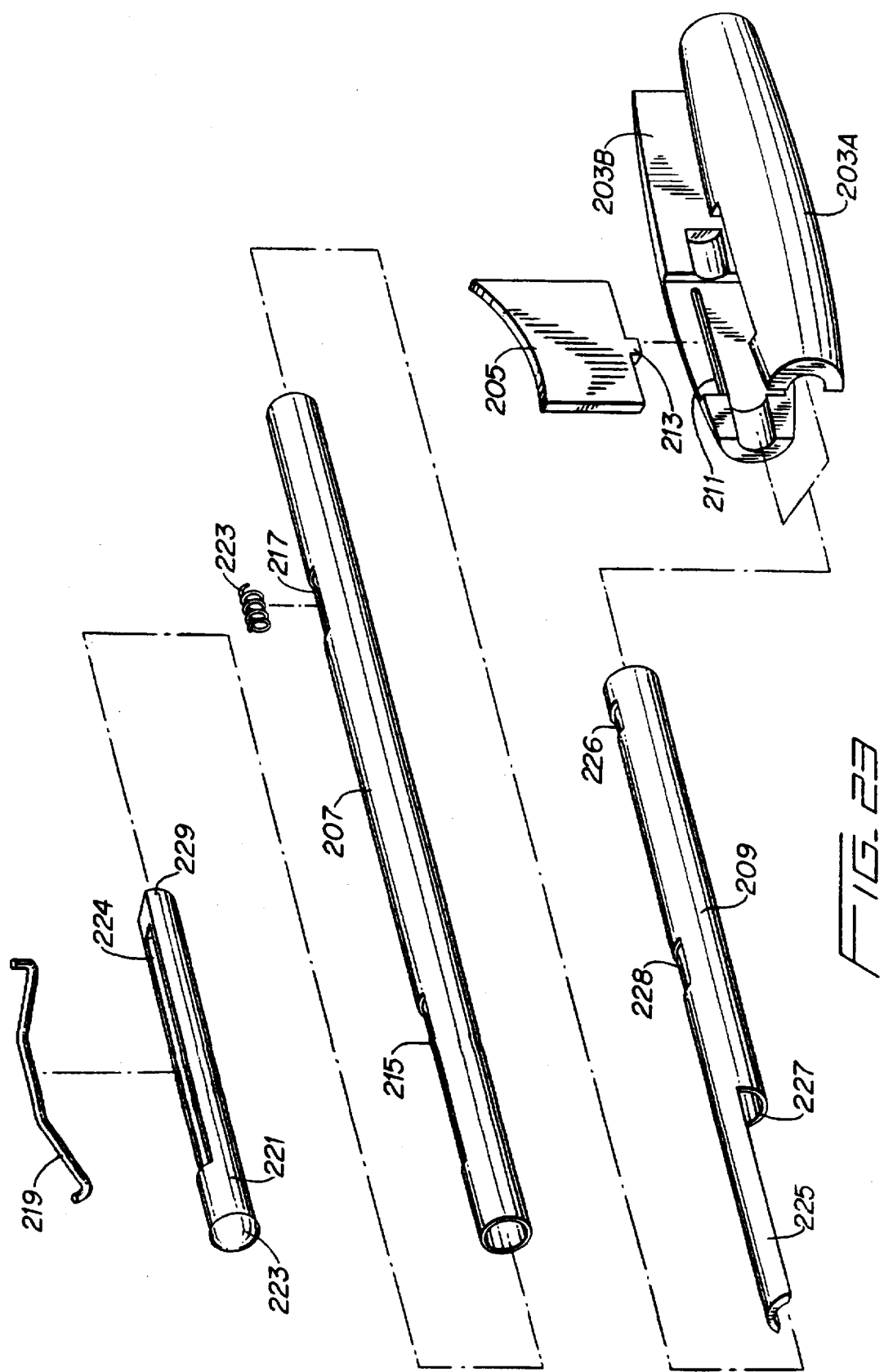

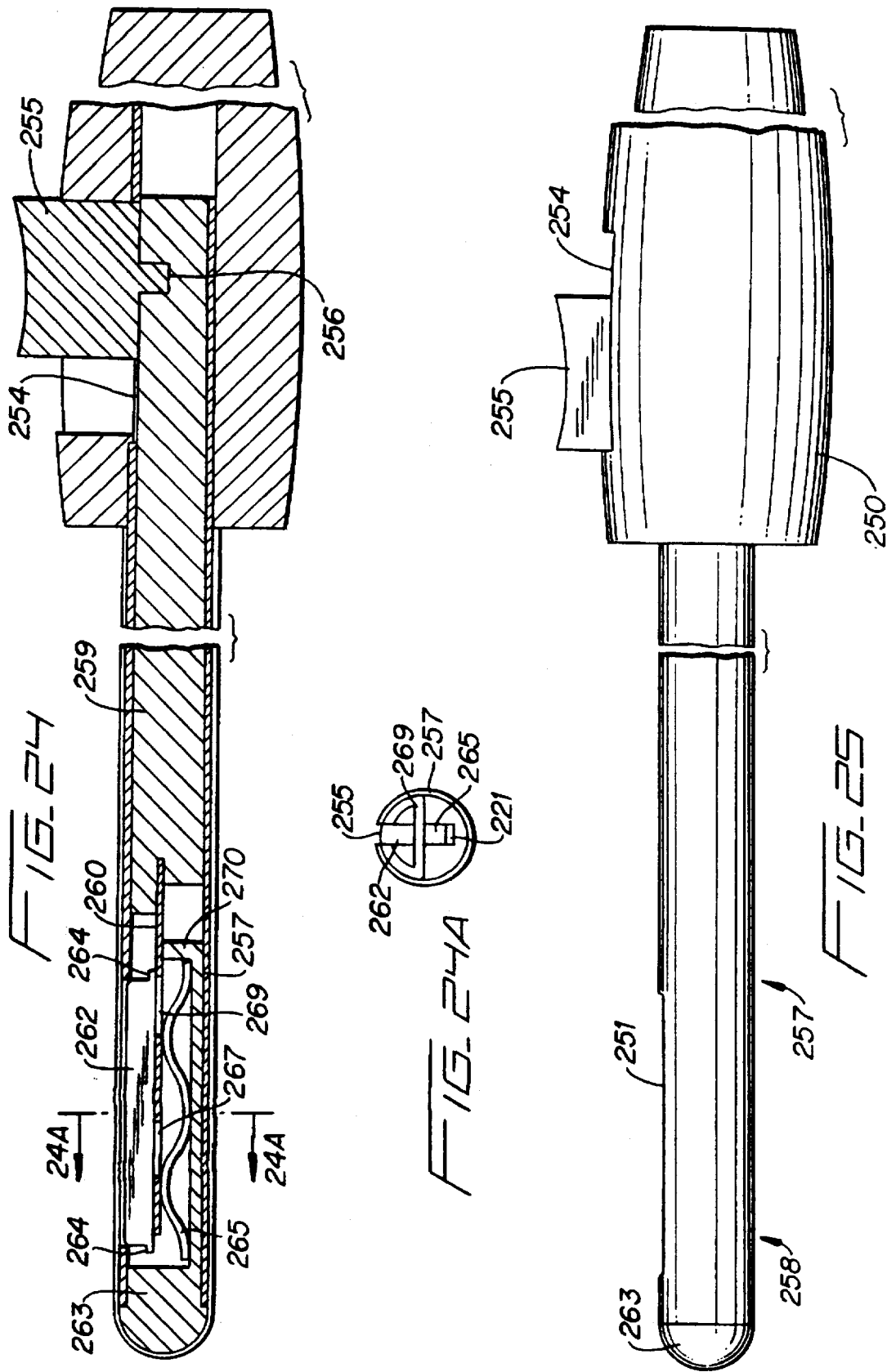

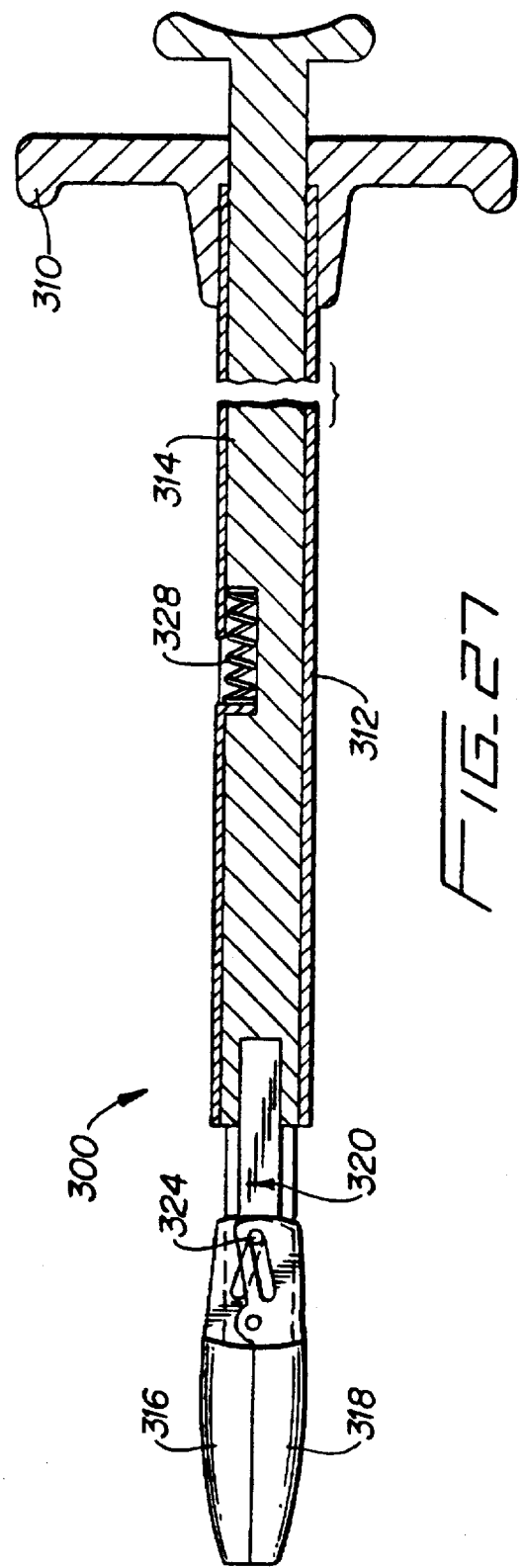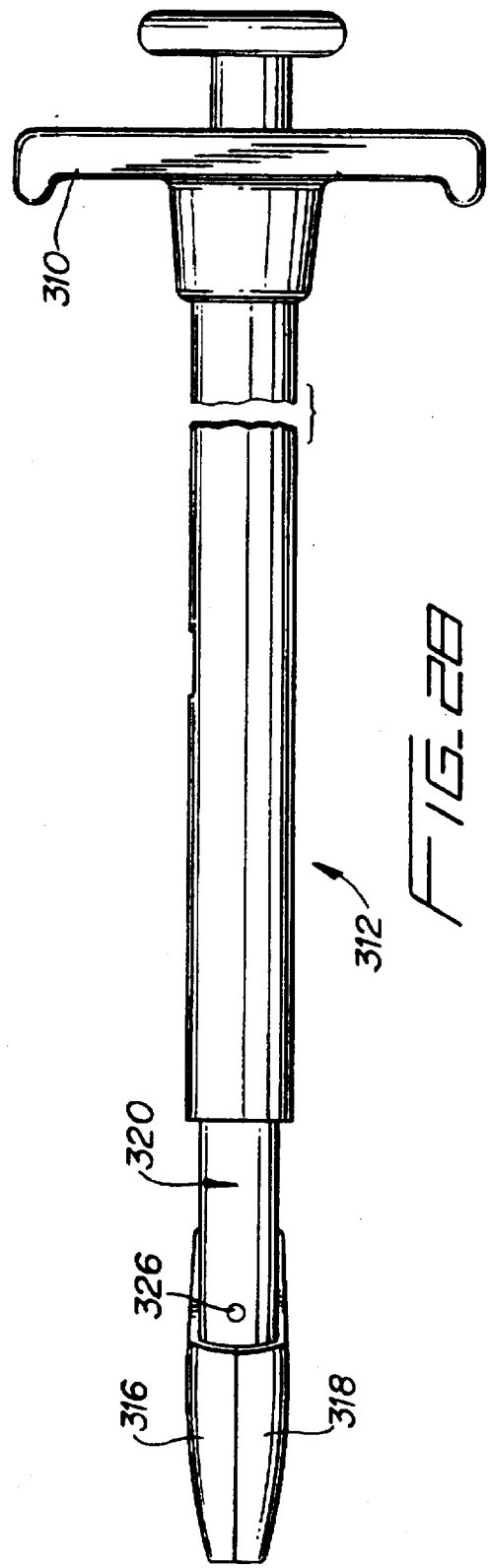

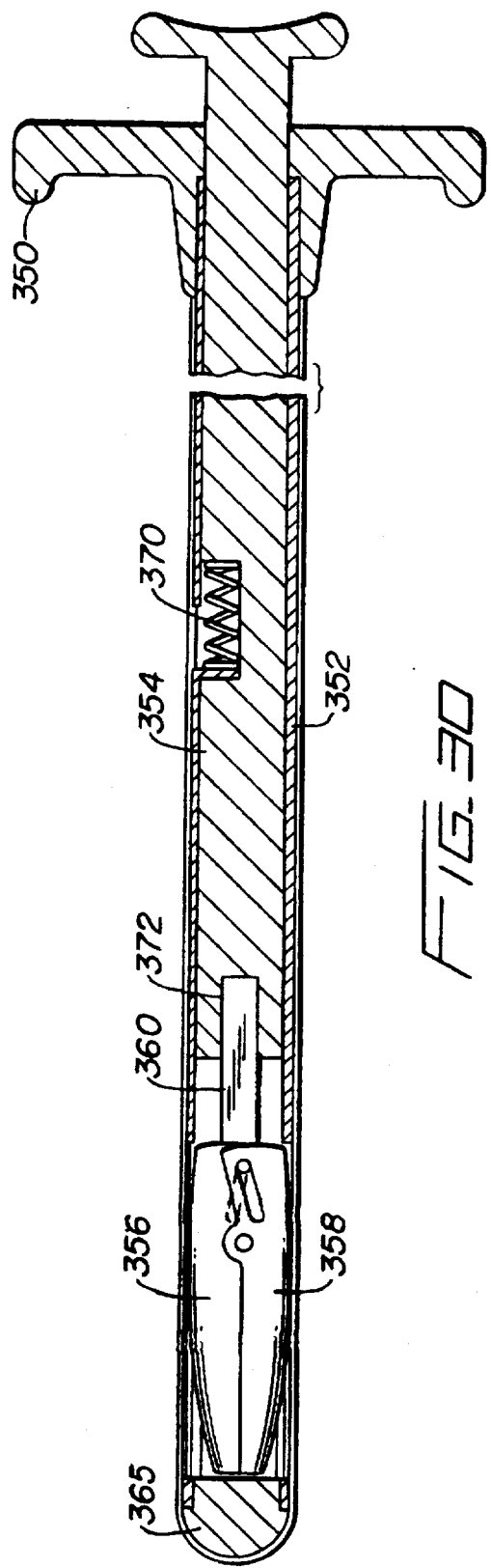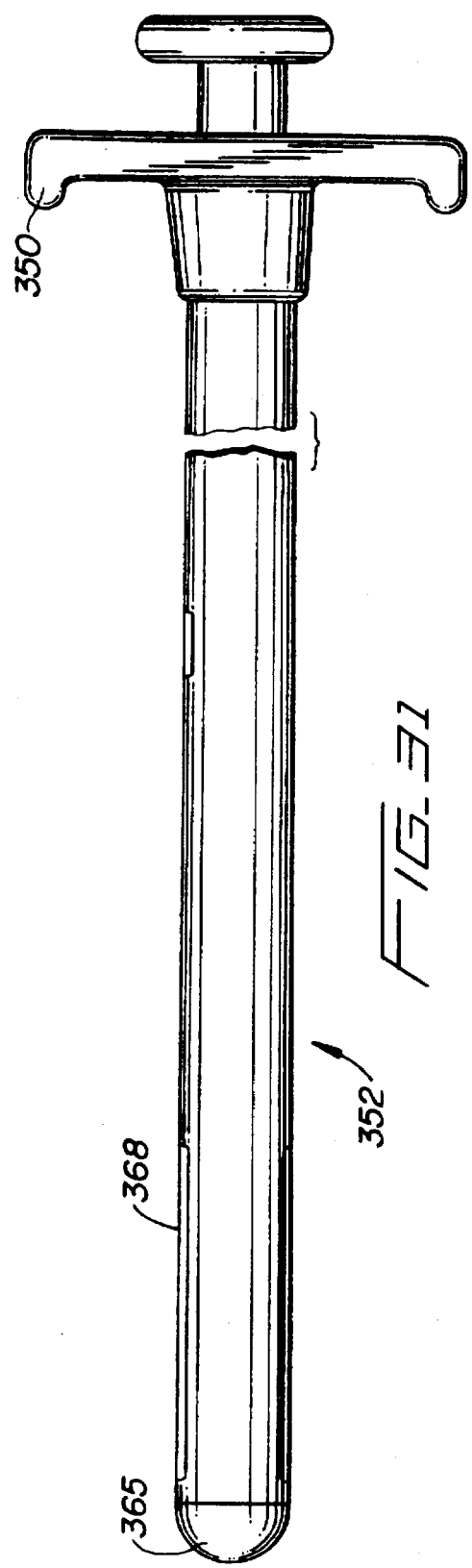

SURGICAL INSTRUMENT FOR EXPANDING BODY TISSUE

This is a divisional of U.S. application Ser. No. 08/124,778 filed Sep. 21, 1993, now abandoned.

BACKGROUND OF THE INVENTION

1. Field of the Invention

The present invention relates to surgical instruments for expanding body tissue, and more particularly to an instrument for expanding ligaments such as the carpal ligament in the hand during surgical procedures such as carpal tunnel release.

2. Discussion of the Related Art

Carpal tunnel syndrome is a condition of the hand which typically results in loss of feeling, weakness or numbness (paresthesia) in the fingers and hand. In general, repetitive, short stroke motion of the fingers and hand may lead to irritation of the median nerve which passes through the carpal tunnel, and this irritation or inflammation may lead to pain, weakness of the muscles and general numbness in the fingers and hand. The carpal tunnel is an area in the hand adjacent the wrist which is bounded by the carpal bones of the hand and the transverse carpal ligament. The median nerve and flexor tendons pass through the tunnel to control movement of the fingers. As the median nerve becomes irritated, or as the transverse carpal ligament is thickened due to repetitive motions of the hand and wrist, compression of the nerve inside the carpal tunnel leads to carpal tunnel syndrome and its associated degenerative conditions.

In order to treat carpal tunnel syndrome, it has been known to cut or divide the transverse carpal ligament, also known as the flexor retinaculum, to provide for decompression of the carpal tunnel. Historically, the division of the transverse carpal ligament was done during open surgical procedures which involved slitting the palm of the hand to expose the ligament prior to cutting the ligament. Recently, instrumentation has been developed to allow this procedure to be performed endoscopically, with a small incision at the base of the wrist to allow for division of the ligament beneath the skin. Once the ligament is cut, it allows for additional space in the carpal tunnel area to relieve the irritation and pressure on the median nerve.

Several instruments are known for performing endoscopic decompression by division of the transverse carpal ligament. An instrument known as the Paine retinaculotome, as described in the Journal of Neurosurgery, Vol. 59, December 1983, pp. 1031–1036, provides a cutting edge which is engagable with the reverse carpal ligament on the wrist side of the ligament. The Paine instrument is inserted into the hand through an incision at the base of the wrist. As the ligament is engaged by the cutting instrument, the instrument is advanced forward into the hand to divide the ligament. A similar instrument is disclosed in U.S. Pat. No. 5,029,573 to Chow which provides a cannula that is inserted into the hand at the base of the wrist and includes a longitudinal slot in the cannula to allow for a cutting instrument to be inserted into the cannula. The instrument may be advanced through the ligament to divide the ligament, or may be inserted into the distal end of the cannula which protrudes from the palm of the patient so that the cutting instrument may be drawn through the ligament as the cutting instrument extends through the slot in the cannula.

As disclosed in U.S. Pat. Nos. 4,962,770, 4,963,147 and 5,089,000 to Agee et al., an endoscopic instrument for performing carpal tunnel release is provided which includes a pivotable cutting blade which extends outside the sheath to effect cutting of the transverse carpal ligament. An endoscope may be provided for viewing the surgical site. A disadvantage of these instruments is that the blade of the cutting instrument is exposed in such a manner that there control of the instrument to prevent cutting of tissues other than the transverse carpal ligament is minimal, and in effect will allow cutting of any tissue which happens to be in the way of the blade.

Furthermore, these known instruments either require the use of numerous components, such as that disclosed in the Chow patent, or provide instruments with numerous moving parts, such as that disclosed in the Agee et al. patents, which reduce the control of the instrument in the confined area of the carpal tunnel.

Other surgical cutting instruments are known which provide for cutting tissue by pinching the tissue between a cutting blade and a wall or stop member of the instrument. Such an instrument is disclosed in U.S. Pat. No. 5,176,695 to Dulebohn which discloses a hook like cutting member which is drawn across a gap in the end of the instrument to hook tissue such as blood vessels. The blood vessels are engaged in the gap against a wall of the instrument to cut the tissue against the wall. Similar instruments are shown in U.S. Pat. No. 3,902,498 to Niederer, U.S. Pat. No. 3,995,619 to Glatzer, and U.S. Pat. No. 4,620,547 to Boebel. A disadvantage of these instruments lies in the fact that they can only cut vessels or other tissues that will fit into the gap so that the tissue may be pinched between the cutting edge and the wall against which the cutting edge is forced.

As disclosed in U.S. Pat. No. 769,829 to Mott, a surgical instrument is provided having a head which houses a rearwardly directed cutting blade which is exposed upon movement of the head away from a housing. As the head is moved away from the housing, an opening or gap is defined between the head and the housing so that the blade may be drawn rearwardly to cut vessels or tissues that are positioned within the gap as the blade moves rearwardly against the housing. This instrument suffers the same disadvantages as the instruments described above which pinch tissue or vessels between the cutting blade and a wall of the instrument.

U.S. Pat. No. 5,179,963 to Berger discloses an alternative method of treating carpal tunnel syndrome which avoids cutting the transverse carpal ligament. In this method, a balloon catheter is inserted with the aid of a director device underneath the transverse carpal ligament. The balloon catheter is serially inflated and deflated while it is moved along the carpal tunnel to stretch the ligament to increase the diameter of the carpal tunnel, thereby relieving compression of the median nerve.

It would be advantageous to have alternative instrumentation which can stretch the carpal tunnel ligament as well as other body structures without requiring an inflatable balloon. Such instrumentation should provide for controllably expanding the carpal tunnel and could provide either expansion of the entire ligament at once or expansion a portion at a time.

SUMMARY OF THE INVENTION

The present invention provides a method for expanding the carpal tunnel during carpal tunnel surgery comprising the steps of providing an instrument having a spring member, inserting the instrument into the carpal tunnel by extending the spring member to extend from the instrument to stretch the carpal tunnel ligament, retracting the spring member and withdrawing the instrument from the carpal tunnel. The spring member can be repeatedly extended and retracted to gradually stretch the ligament by actuating a handle member connected to the instrument body. The step of extending the spring member preferably simultaneously stretches a membrane positioned on the instrument.

A method for expanding the carpal tunnel by stretching the carpal ligament during carpal tunnel surgery is also provided comprising the steps of providing an instrument having a housing portion, a substantially rigid member and a membrane, inserting the instrument into the carpal tunnel, and actuating the instrument to extend the rigid member from the housing to contact and stretch the membrane to stretch the carpal ligament. The member is then retracted toward the housing to retract the membrane and the instrument is withdrawn from the carpal tunnel. The step of actuating the instrument can comprise the step of camming the substantially rigid member through an aperture in the instrument.

An apparatus for expanding the carpal tunnel ligament during carpal tunnel surgery is also provided. The apparatus includes an elongated body portion having a longitudinal opening formed therein, a spring member positioned within said body and movable between a first position substantially contained within said body portion and a second position protruding through the opening to contact and stretch the body tissue, and means for controllably moving the spring member between the first and second positions. The apparatus further comprises a flexible membrane positioned over at least a portion of the elongated body portion. Means for moving the spring member in a first direction toward said second position and means for preventing extension of said spring member in a direction opposite to said first direction can also be provided.

The present invention can also provide an apparatus for expanding the carpal tunnel ligament during carpal tunnel surgery comprising an elongated body portion having at least one aperture formed in an outer surface with at least one substantially rigid member positioned in said body portion and movable between a retracted position and an extended position. The rigid member extends through the aperture and protrudes beyond the outer surface when moved to the extended position. Means for controllably moving said rigid member between the retracted and extended positions is provided. The apparatus further includes a flexible membrane positioned over at least a portion of said elongated body portion and expandable upon movement of the substantially rigid member to the extended position. The elongated body portion is preferably substantially circular in cross section and has a longitudinal axis dividing said body portion into first and second sections, wherein the substantially rigid member moves only in said first section. A plunger, longitudinally movable in said body portion, can move said substantially rigid member.

The apparatus for expanding body tissue may also comprise an elongated member having a predetermined peripheral portion, wherein the predetermined peripheral portion defines only a segment of the peripheral portion. A first member is positioned in the elongated member for movement between a first retracted position and a second extended position to stretch body tissue and a membrane is positioned over at least a portion of said elongated member. Means is positioned within said elongated member for moving the first member from the extended position to the retracted position to expand the membrane, the first member being extended only towards the predetermined peripheral portion.

BRIEF DESCRIPTION OF THE DRAWINGS

Preferred embodiments of the invention are described here and below with reference to the drawings wherein:

FIG. 1 is a perspective view of a first embodiment of the present invention utilizing a plunger handle for deploying the membrane;

FIG. 2 is a side view of the apparatus of FIG. 1 with the plunger in the extended (undeployed) position;

FIG. 3 is a cross-sectional view of the apparatus of FIG. 2;

FIG. 3A is a cross-sectional view taken along lines 3A—3A of FIG. 3;

FIG. 4 is a cross-sectional view of the apparatus of FIG. 1 in the deployed position;

FIG. 5 is an alternate embodiment of the handle mechanism utilizing a slide button mechanism for deploying the membrane;

FIG. 6 is another alternate embodiment of the handle mechanism, in the form of a pistol grip, for deploying the membrane;

FIG. 7 is a cross-sectional view of an alternate embodiment of the apparatus of the present invention, shown in the undeployed position;

FIG. 7A is a cross-sectional view taken along line 7A—7A of FIG. 7;

FIG. 8 is a side view of the apparatus of FIG. 7;

FIG. 9 is a cross-sectional view of the apparatus of FIG. 7 showing the plunger depressed and the instrument in the deployed position;

FIG. 10 is a cross sectional view of another alternate embodiment of the instrument of the present invention, shown with the plunger and membrane in the undeployed position;

FIG. 10A is a cross-sectional view taken along lines 10A—10A of FIG. 10;

FIG. 11 is a side view of the apparatus of FIG. 10;

FIG. 12 is a cross-sectional view of the apparatus of FIG. 10 in the deployed position;

FIG. 13 is yet another alternate embodiment of the apparatus of the present invention for deploying a membrane, shown in the undeployed position;

FIG. 13A is a cross-sectional view taken along lines 13A—13A of FIG. 13;

FIG. 14 is a side view of the apparatus of FIG. 13;

FIG. 15 is a cross-sectional view of the apparatus of FIG. 13 showing the plunger and membrane in the deployed position;

FIG. 16 is still another alternate embodiment of the apparatus for deploying a membrane in accordance with the present invention, shown in the undeployed position;

FIG. 16A is a cross-sectional view taken along lines 16A—16A of FIG. 16;

FIG. 17 is a cross-sectional view of the apparatus of FIG. 16 showing the plunger depressed and the membrane in the deployed position;

FIG. 18 is a cross-sectional view of yet another alternate embodiment of the apparatus of the present invention showing the plunger in the extended position and the membrane in the undeployed position;

FIG. 18A is a cross-sectional view taken lines 18A—18A of FIG. 18;

FIG. 20 is a side view of another alternate embodiment of an apparatus for deploying a membrane utilizing a slide button mechanism;

FIG. 21 is a cross-sectional view of the apparatus of FIG. 20 showing the apparatus in the undeployed position;

FIG. 21A is a cross-sectional view taken along lines 21A—21A of FIG. 21;

FIG. 23 is an exploded perspective view of the apparatus of FIG. 20;

FIG. 24 is a cross-sectional view of yet another alternate embodiment of the apparatus for deploying a membrane utilizing a slide button mechanism, the apparatus being shown in the undeployed position;

FIG. 24A is a cross-sectional view taken along lines 24A—24A of FIG. 24;

FIG. 25 is a side view of the instrument of FIG. 24 shown in the deployed position;

FIG. 27 is still another alternate embodiment of the apparatus of the present invention utilizing a pair of jaws to stretch the body tissue, the jaws being shown in the closed position;

FIG. 28 is a side view of the instrument of FIG. 27;

FIG. 30 is a cross-sectional view of yet another alternate embodiment of an apparatus of the present invention utilizing a pair of jaws for deploying a membrane, the jaws being shown in the closed position housed within the apparatus;

FIG. 32 is a cross-sectional view of the apparatus of FIG. 30 showing the jaws in the open deployed position.

DETAILED DESCRIPTION OF THE PREFERRED EMBODIMENTS

Figure 19:
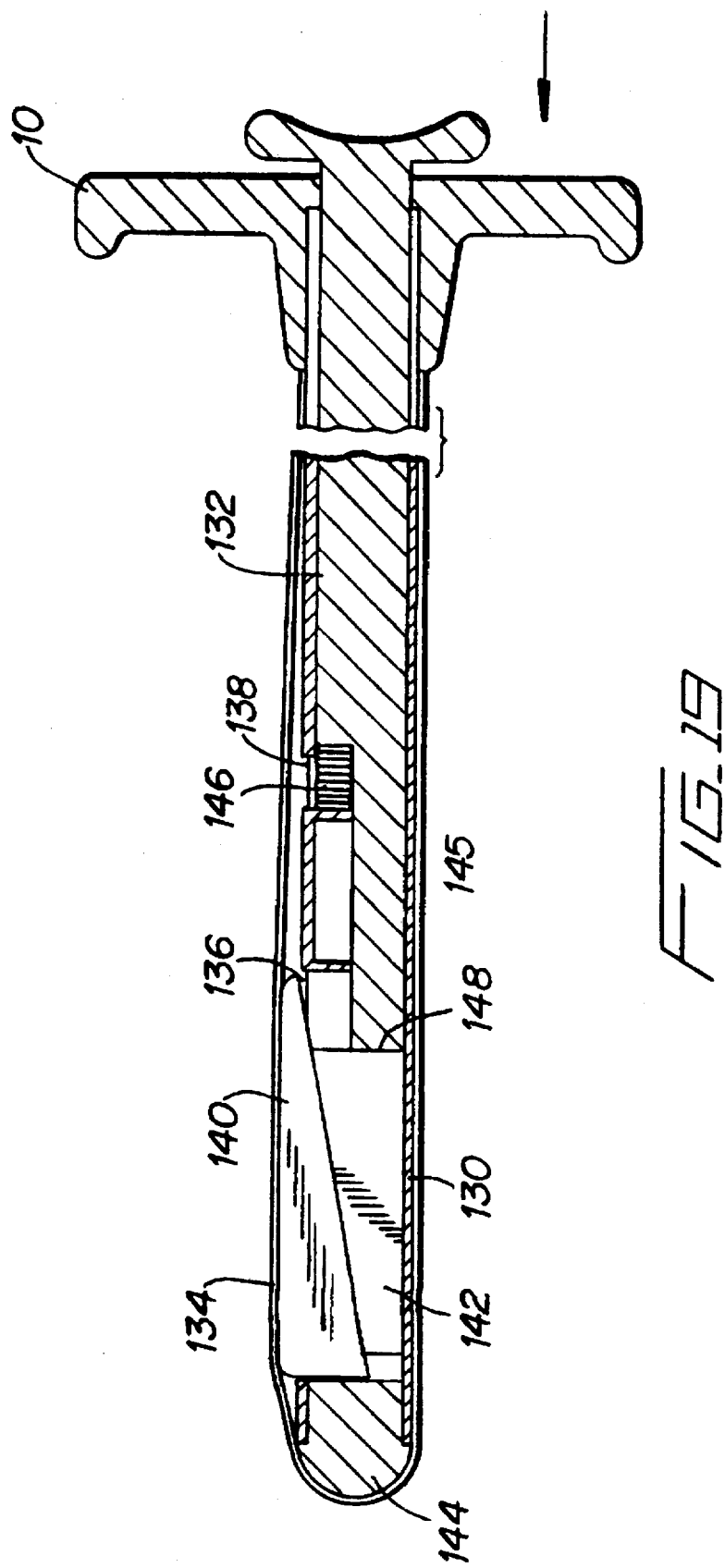
FIG. 19 is a cross-sectional view of the apparatus of FIG. 18 showing the membrane in the deployed (expanded) position.

Referring now to the drawings, in which like reference numerals identify similar or identical elements, FIG. 1 illustrates a first embodiment of the apparatus of the present invention designated generally by reference numeral 1. The instrument 1 includes a handle or grip portion 10, an elongated body portion 12 extending from the handle 10, and a plunger 14 slidably disposed therein. A membrane 16 is disposed over the body portion 12. (It should be noted that for purposes of clarity, the membrane is not shown in all the Figures of each of the embodiments discussed below.) The elongated body portion includes a distal portion 13, a proximal portion 15 and apertures 18 and 20. As shown in FIG. 3, a cam plate 24 is attached to body portion 12 by fixed pin 28. Cam plate 24 also includes camming slot 27 in which camming pin 26, attached to plunger 14, slides. An overhang 30 extends downwardly towards a center longitudinal axis of the instrument to provide a stop for the spring 34. Plunger 14 is slidably positioned in the longitudinally extending bore of the elongated body portion 12 and is spring biased proximally to an extended position by spring 34.

In use, in the at rest (undeployed) position shown in FIG. 3 the cam plate 24 is positioned entirely within the body portion 12. Upon movement (depression) of the plunger distally from its extended position in the direction of the arrow in FIG. 4, camming pin 26 slides distally along cam slot 27 to force cam plate 27 upwardly through aperture 18 thereby stretching, i.e. expanding, the membrane 16. Upon release of plunger 14, spring 34 moves from its compressed position of FIG. 4 to its normal position, thereby returning the plunger 14 to its initial position and allowing cam plate 24 to return to the original position of FIG. 3.

FIG. 5 illustrates an alternate embodiment of the apparatus of FIG. 1 utilizing a slide button 5 which protrudes outwardly from elongated handle 3 and slides within slot 4. The slide button 5 is operatively connected to a slide rod (or plunger) for moving the cam plate to deploy the membrane. In the alternate embodiment of FIG. 6, a movable handle 7 pivots in relation to stationary grip portion 8. Movable handle 7 is operatively connected to a slide rod (or plunger) for actuating the cam plate and expanding the membrane as discussed above with respect to FIG. 3. Note that not only these handle mechanisms, but any other mechanisms for reciprocating a rod, can be utilized with the embodiment of FIGS. 1–4 as well as with the alternate mechanisms for deploying the membrane which are discussed in detail below.

FIGS. 7–9 illustrate an alternate embodiment for expanding membrane 16. Plunger 40 has an abutment surface 44 adapted to contact lift plate 46 to force it upwardly through aperture 18 in elongated body potion 12. As shown, lift plate 46 is pivotally attached to end cap 22 of the body portion 12 by pivot pin 48. Upon movement of plunger 40 distally in the direction of the arrow of FIG. 9, abutment surface 44 cams lift plate 46 upwardly through aperture 18; lift plate 46 pivoting around pivot pin 48 and compressing spring 50. Distal movement of the plunger 40 also compresses spring 42 against overhang 30. Upon release of the plunger 40, spring 42 forces the plunger 42 toward its original position and spring 50 causes lift plate 46 to return to its original at rest position of FIG. 7.

In the embodiments of FIGS. 1–9, the pivoting plates extend through a small aperture in the elongated body portion so that a smaller portion of the membrane is fully extended and the stretching force is applied against a relatively small area of the body tissue. If desired, the instrument can be advanced or retracted with the membrane deployed to continuously stretch the body tissue or alternatively, the membrane can be repeatedly deployed (expanded) and retracted to intermittently stretch the body tissue. In FIGS. 10–19, the distal aperture in the elongated member is longer than in FIG. 1–9 to provide a larger area of contact with the membrane. This allows for expansion of a larger portion of the body tissue, and if of sufficient length, can avoid, if desired, the necessity of continuous or intermittent stretching of body tissue by expanding the entire body structure in a single gradual deployment of the membrane.

Turning now in detail to the embodiment of FIGS. 10–12, elongated body portion 60 extends from handle 10 and has a longitudinal bore for slidably receiving plunger 62. Elongated aperture 66 and proximal aperture 68 are formed in the body portion and the body portion is covered by membrane 64. Leaf spring 61 is positioned within the body portion and has a distal leg frictionally positioned in recess 69 of end cap 63. The proximal leg is positioned within recess 67 of plunger 62. Upon movement of plunger 62 distally in the direction of the arrow of FIG. 12, the leaf spring 61 is compressed such that the upper portion is forced outwardly through elongated aperture 66 to stretch (expand) membrane 64. Compression spring 65 biases the plunger to its proximal at rest position in the same manner as discussed with the embodiment of FIG. 1.

In FIGS. 13–15, elongated body member 70, extending from handle 10, has end cap 80, and elongated aperture 76 and proximal aperture 78. Plunger 72, slidably received in the longitudinal bore of the elongated member 70, includes a spring 92 biasing it to the at rest (extended) position and further has a slot 94 at its distal end to receive pin 84.

Elongated plate 82, preferably in the shape of a parallelogram, has a lower portion 83 with longitudinally extending pin 84 extending into slot 94 of plunger 72. A series of cam plates 86, preferably three as shown in FIG. 13 although additional or fewer cam plates can be utilized, are positioned within elongated member 70. More specifically, plate pin 88 connects the upper end of each cam plate 86 to lower portion 83 of elongated plate 82 and housing pins 89 connect the lower end of each cam plate 86 to the inner support 85. (For clarity, only one pin 89 is numbered in FIGS. 13 and 15.) Step 96 of plunger 72 is adapted to come into contact with stop 91 of inner support 95 to limit movement of plunger 72.

In use, distal movement of plunger 72 forces elongated plate 82 to pivot counterclockwise as cam plates 86 are rotated to the vertical position shown in FIG. 15. Longitudinal pin 84 slides to the upper portion of slot 94 in plunger 72. Elongated plate 82 slides through aperture 86 to stretch membrane 74. Spring 92 operates in a similar manner as discussed above with respect to FIG. 1 in biasing the plunger proximally.

FIGS. 16 and 17 illustrate an alternate embodiment using a plate 116 having cam slots 118 and camming pin 120. Positioned within elongated body portion 101 is end cap 110 and spring retaining wall 114, with spring 112 positioned therebetween to bias spring retaining wall 114 proximally.

Upon distal movement of plunger 102 in the direction of the arrow of FIG. 17, cam plate 116 is forced distally and upwardly to the position shown in FIG. 17 due to angled cam slots 118. This upward movement of cam plate 116 through aperture 106 stretches membrane 104. This distal movement of cam plate 116 forces spring retaining wall 114 distally towards end cap 110 thereby compressing spring 112. Upon release of plunger 102, spring 126 and spring 112 operate to return the plunger and cam plate 116 to the at rest position of FIG. 16.

In the alternate embodiment of FIGS. 18 and 19, elongated body portion 130 includes an upper plate 140 and a lower camming plate 142 positioned between end cap 144 and abutting wall 148 of plunger 132. The dovetail fitting of the plates 140 and 142 can be seen in FIG. 18A. Upon distal movement plunger 132 in the direction of the arrow of FIG. 19, lower cam plate 142 is slid distally, thereby camming upper plate 140 upwardly through the aperture in the elongated body portion to contact and expand (stretch) the membrane 134. Spring 146 biases the plunger to the proximal at rest position in the same manner described upon with the other embodiments. Optionally, a spring can also be provided to bias lower cam plate 142 proximally.

FIGS. 20–23 illustrate an alternative apparatus for expanding a membrane utilizing a slide button mechanism. More specifically, the instrument has a elongated grip portion 203, a slot 204 to allow movement of slide button 205, an elongated body portion 207 having elongated aperture 215 and proximal aperture 217, and a membrane 206.

With reference to FIG. 23, handle 203 includes opposing housing halves 203 and 203B, with housing half 203B having an elongated slot 211 to receive projection 213 of slide button 205.

Elongated body portion 207 has a support member 223, and a spring 219 positioned at the distal end portion 214. Support member 223 has a recess 224 to receive spring 219.

Slide plate 209 is positioned within body portion 207 for longitudinal reciprocal movement therein and is biased to a distal position by spring 223. Wall 229 of support member 223 acts as a stop for slide plate 209 as it is contacted by step 227. Aperture 226 of slide plate 209 receives projection 213 of button 205 such that movement of button 205 carries slide plate 209 in the same direction. Spring 223 is positioned in aperture 228.

Figure 22:
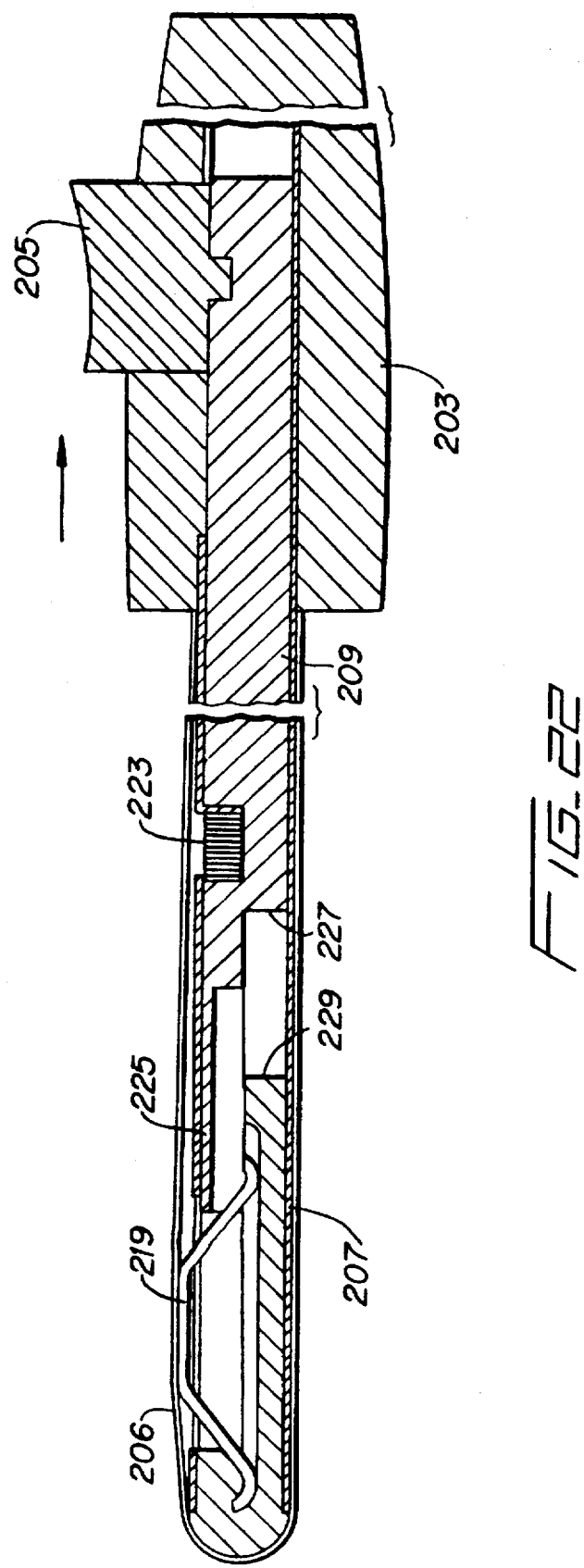
FIG. 22 is a cross-sectional view of the apparatus of FIG. 20 showing the apparatus in the deployed position.

In use, in the initial position, retaining wall 225 of slide plate 209 is positioned over spring 219 to forceably retain it in the flattened positioned of FIG. 21. Upon proximal movement of slide button 205 in the direction of the arrow in FIG. 22, the slide plate 209 is likewise pulled proximally so that retaining wall 225 is slid rearwardly to free spring 219 to allow it to move to its normal extended position. In this extended position, spring 219 extends through aperture 215 to stretch membrane 206. Such movement of slide button 205 to the deployed position compresses spring 223 as shown in FIG. 22. Upon release of the slide button 205, slide plate 209 is forced distally by spring 223 to its original position, thereby forcing spring 219 to the position of FIG. 21 as it is cammed downwardly by retaining wall 225. Spring 219 can be composed of memory metal or other materials so that the position of FIG. 22 is its normal position and it is constrained by retaining wall plate 209.

Figure 26:
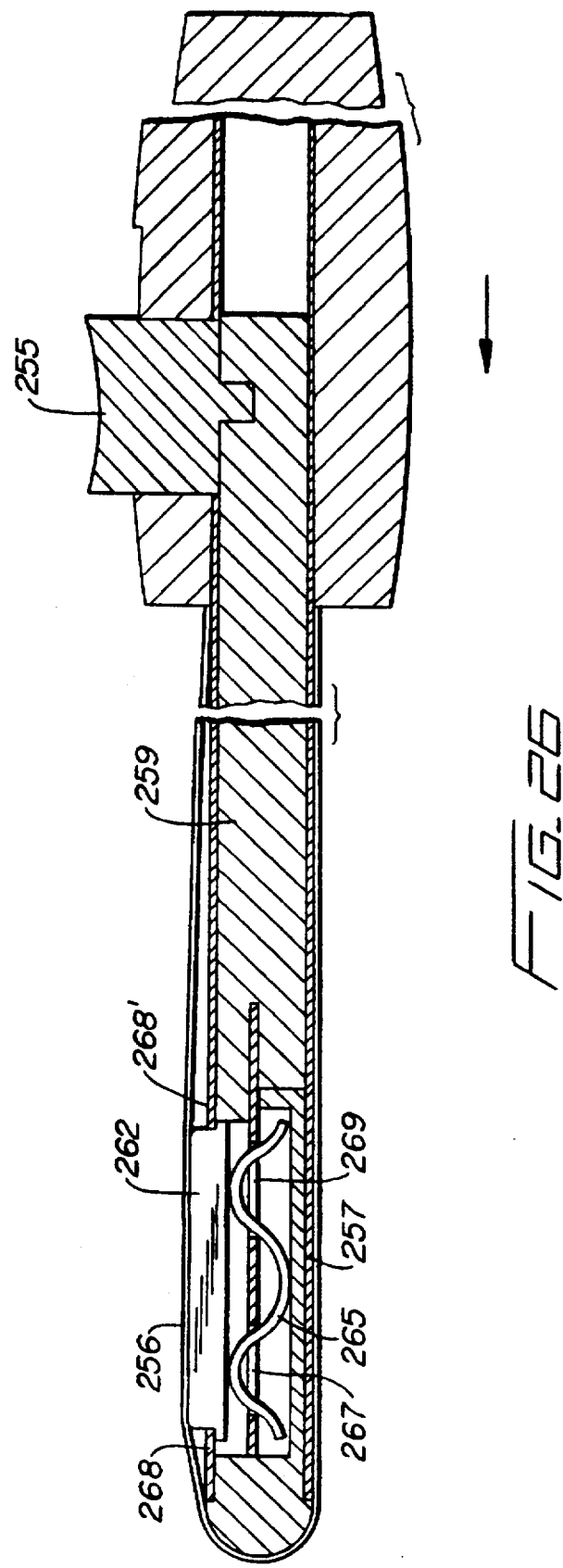
FIG. 26 is a cross-sectional view of the apparatus of FIG. 24 shown in the deployed position.
Figure 29:
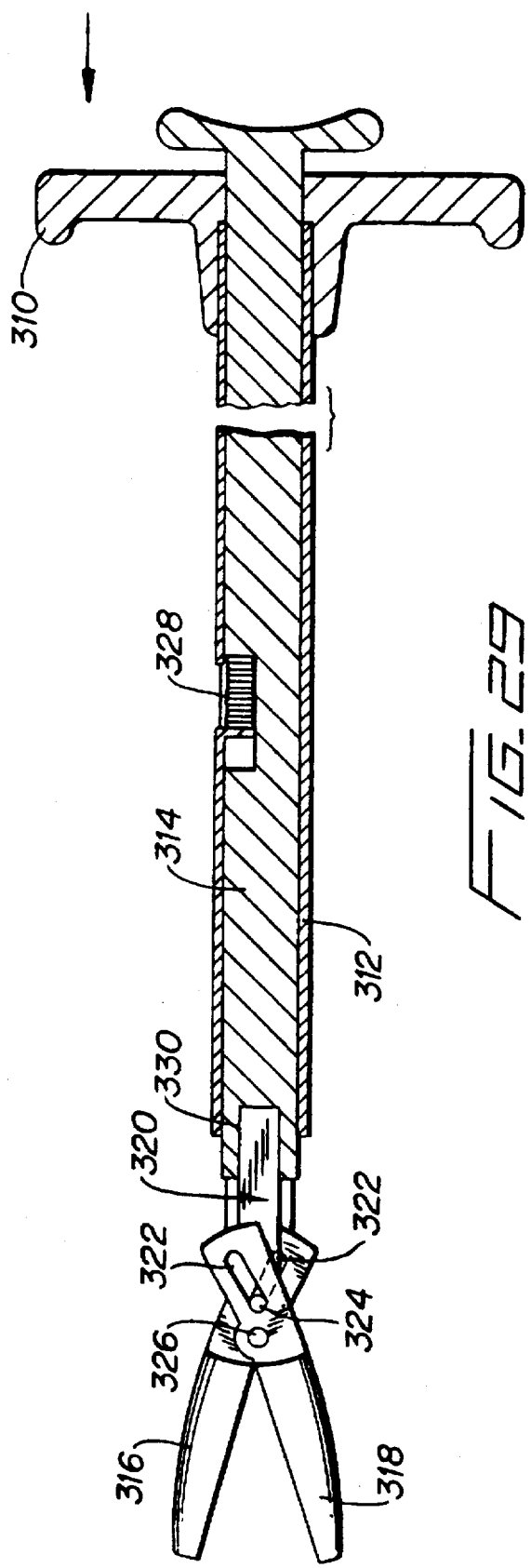
FIG. 29 is a cross-sectional view of the apparatus of FIG. 28 showing the jaws in the open position.

FIGS. 24–26 illustrate an alternate embodiment of an apparatus for deploying a spring member utilizing a slide button. More specifically, slide button 255 extends through slot 254 in elongated handle 250 and is connected to plunger 259 via projection 256. Elongated body portion 257 has a distal portion 258, end cap 263 and elongated aperture 251.

Positioned within body portion 257 is a plate 260 having apertures 267 and 269. Pad 262, preferably composed of a soft compressible material, is positioned atop plate 260. Pad 262 has flange 264 for contact with walls 268 and 268' when the spring is deployed. End cap 263 terminates at its proximal end with a stop 270 to limit distal movement of plunger 259.

In use, slide button 255 is slid distally in the direction of the arrow to the position of FIG. 26. This sliding movement of plunger 259 moves plate 260 distally, thereby aligning apertures 267 and 269 with the raised portions of spring 265. As the raised portions project through the apertures, they force pad 262 upwardly into contact with the membrane 256 to stretch the membrane. Upward movement of pad 262 is limited by the contact of flange 264 with walls 268, 268'. When plate 260 is pulled proximally by slide button 255, the raised portions of the spring 265 are cammed downwardly by plate 260 and then retained by the solid surface portions of the plate, thereby allowing pad 262 to return to its at rest position of FIG. 24.

As can be seen, each of these instruments provide mechanical means for expanding a membrane to expand or stretch a body portion. When used in carpal tunnel surgery, it stretches the transverse carpal ligament to expand the carpal tunnel, thus relieving pressure on the median nerve. Preferably, the membrane is expandable only upwardly from the central longitudinal axis. That is, the spring or substantially rigid cam plate preferably moves in one direction, e.g. away from a central longitudinal axis, so that the membrane is expandable around less than a 360° peripheral portion of the tubular elongated member. The instruments of the present invention can also be utilized for procedures other than carpal tunnel surgery which require stretching body structures. The instruments of the present invention also allow for controlled, and progressive if desired, stretching of the membrane by the surgeon controlling the distance of travel of the reciprocating slide rod.

FIGS. 27-32 illustrate yet other alternate embodiments of the apparatus utilizing a pair of jaws for stretching the body portion. With reference first to the embodiment of FIGS. 27-29, instrument 300 has a handle 310, a body portion 312 extending therefrom and a plunger of 314 positioned for longitudinal reciprocal movement therein. A pair of jaws 316, 318 are connected to drive rod 320 which extends distally from cutout 330 of plunger 314. Upon distal movement of plunger 314 in the direction of the arrow of FIG. 29, drive rod 320 is moved distally, thus allowing camming pin 324 to travel in angled cam slots 322 forcing the jaws to pivot around pivot pin 326 to the open position. Spring 328 biases the plunger proximally to the at rest position of FIG. 27. Alternatively, the jaws can be configured so that one of the jaws is stationary and only one of the jaws is movable. A membrane can optionally be placed around the jaws.

Figure 32:
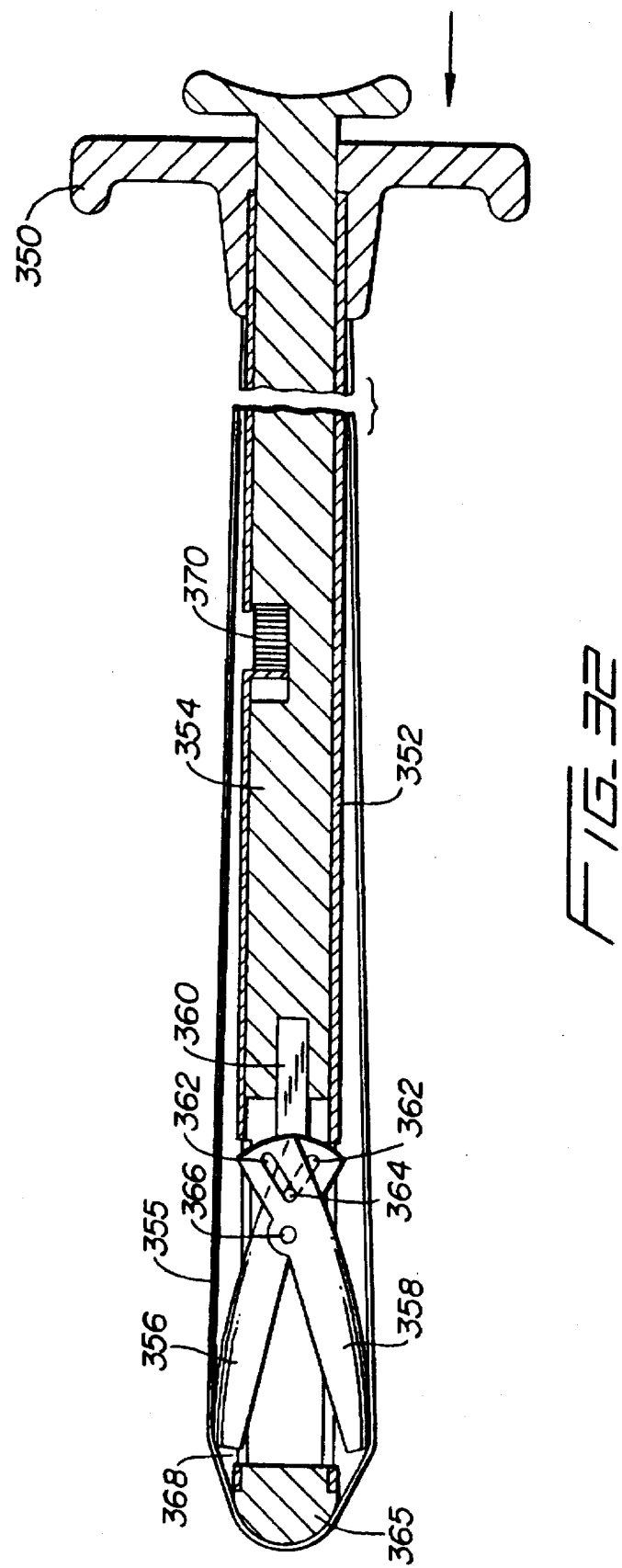
FIG. 32 is a side view of the apparatus of FIG. 30.

In the alternate embodiment of FIGS. 30-32, the jaws are contained wholly within the elongated body portion until deployed. As shown, body portion 352 extends from handle 350 and has a longitudinal bore to receive plunger 354 for reciprocal movement therein. Drive rod 360 is positioned within cutout 372 of plunger 370. Upon distal movement of plunger 354 in the direction of the arrow of FIG. 32, the drive rod 360 carries camming pin 364 distally in angled cam slots 362 to open the jaws as shown in FIG. 32 as they pivot around pivot pin 366. This stretches the membrane 355. Spring 370 functions in the manner as described above with respect to FIG. 27 in biasing the plunger proximally.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An apparatus for expanding the carpal tunnel ligament during carpal tunnel surgery comprising:
   a) an elongated body portion having at least one aperture in an outer surface thereof;
   b) at least one spring member positioned within said body portion and movable between a first position substantially contained within said body portion and a second position protruding through said aperture to contact and stretch body tissue;
   c) means for controllably moving said spring member between said first and second positions; and
   d) a flexible membrane disposed over at least a portion of said body portion adjacent said aperture, said spring member engaging said flexible membrane upon movement of said spring member to said second position thereof to cause stretching of said flexible membrane whereby said flexible membrane engages the tissue.

2. The apparatus of claim 1, further comprising means for moving said spring member in a first direction towards said second position and means for preventing movement of said spring member in a direction opposite to said first direction.

3. The apparatus of claim 1 wherein said means for controllably moving said spring member includes a movable member extending through said body portion and engageable with said spring member wherein said spring member moves between said first and second positions thereof in response to corresponding movement of said movable member.

4. The apparatus of claim 3 wherein said moveable member includes a plunger operatively connected to said spring member and longitudinally movable in said body portion for moving said spring member between said first and second positions thereof.

5. The apparatus of claim 3 wherein said first position of said spring member corresponds to an unstressed condition of said spring member and wherein said second position of said spring member corresponds to a stressed condition of said spring member.

6. The apparatus of claim 3 wherein said first position of said spring member corresponds to a stressed condition of said spring member and wherein said second position of said spring member corresponds to an unstressed condition of said spring member.

7. The apparatus of claim 6 wherein said movable member is a slide member, said slide member at least partially extending within said body portion and being movable between first and second positions, wherein movement of said slide member to said first position thereof causes said slide member to engage said spring member to cause said spring member to assume its stressed condition contained within said body portion, wherein movement of said slide member to said second position thereof causes said slide member to disengage said spring member to permit said spring member to assume its unstressed condition protruding through said aperture of said body portion to engage and stretch adjacent body tissue.

8. The apparatus according to claim 3 further including a support pad disposed adjacent said spring member, said support pad engaged by said spring member upon partial movement of said spring member to said second position thereof such that said support pad at least partially extends beyond said outer surface of said elongated body portion to contact and stretch body tissue.

9. The apparatus according to claim 8 wherein said pad member is fabricated of compressible material.

10. An apparatus for expanding the carpal tunnel ligament during carpal tunnel surgery, which comprises:
   a) an elongated body portion having at least one aperture in an outer surface thereof;
   b) at least one spring member positioned within said body portion and movable between a first position substantially contained within said body portion and a second position protruding through said aperture to contact and stretch body tissue;
   c) a movable member extending through said body portion and engageable with said spring member wherein said spring member moves between said first and second positions thereof in response to corresponding movement of said movable member; and
   d) a handle member connected to a proximal end portion of said body potion, said handle member including a pivotable member operatively connected to said moveable member, wherein movement of said pivotable member moves said moveable member to cause corresponding movement of said spring member between said first and second positions thereof.

11. An apparatus for expanding the carpal tunnel ligament during carpal tunnel surgery, which comprises:
   a) an elongated body portion having at least one aperture in an outer surface thereof;
   b) at least one spring member positioned within said body portion and movable between a first position substantially contained within said body portion and a second position protruding through said aperture to contact and stretch body tissue;

c) a movable member extending through said body portion and engageable with said spring member wherein said spring member moves between said first and second positions thereof in response to corresponding movement of said movable member; and d) a handle member connected to a proximal end portion of said body portion, said handle portion including a slide button slidably mounted to said handle member and operatively connectable to said moveable member wherein movement of said slide button moves said moveable member to cause corresponding movement of said spring member between said first and second positions thereof.

12. An apparatus for expanding the carpal tunnel ligament during carpal tunnel surgery, which comprises:

a) an elongated body portion having at least one aperture in an outer surface thereof;

b) at least one spring member positioned within the body portion and movable between a first position substantially contained within the body portion and a second position protruding through the aperture to contact and stretch body tissue, the first position of the spring member corresponding to a stressed condition of the spring member, the second position of the spring member corresponding to an unstressed condition of the spring member; and c) a movable member at least partially extending through the body portion and engageable with the spring member, the slide member being movable between first and second positions, wherein movement of the slide member to the first position thereof causes the slide member to engage the spring member to cause the spring member to assume its stressed condition contained within the body portion, wherein movement of the slide member to the second position thereof causes the slide member to disengage the spring member to permit the spring member to assume its unstressed condition protruding through the aperture of the body portion to engage and stretch adjacent body tissue.

13. An apparatus for expanding the carpal tunnel ligament during carpal tunnel surgery, which comprises:

a) an elongated body portion having at least one aperture in an outer surface thereof;

b) at least one spring member positioned within the body portion and movable between a first position substantially contained within the body portion and a second position protruding through the aperture to contact and stretch body tissue;

c) a movable member extending through the body portion and engageable with the spring member wherein the spring member moves between the first and second positions thereof in response to corresponding movement of the movable member; and d) a handle member connected to a proximal end portion of the body portion, the handle member including a frame and a manually actuable member mounted to the frame and movable relative thereto, the manually actuable member operatively connected to the moveable member wherein movement of the actuable member moves the moveable member to cause corresponding movement of the spring member between the first and second positions thereof.

14. A method for expanding the carpal tunnel ligament during carpal tunnel surgery comprising the steps of:

a) providing an instrument including an elongated body portion having a spring member positioned therein and being movable with respect to the elongated portion, and a moveable member operatively connected to the spring member;

b) inserting at least a portion of the instrument into the carpal tunnel;

c) actuating the moveable member to cause movement of the spring member in a first direction such that at least a portion of the spring member at least partially extends from the instrument to stretch the carpal tunnel ligament;

d) moving the moveable member in a second direction to cause corresponding retraction of the spring member; and e) withdrawing the instrument from the carpal tunnel.

15. The method of claim 14, wherein steps (c) and (d) are repeated a plurality of times such that the spring member is repeatedly at least partially extended and retracted to gradually stretch the ligament.

16. The method of claim 15, wherein the step of actuating the moveable member includes actuating a handle member operatively connected to the movable member.

17. The method of claim 14, wherein the step of providing the instrument includes positioning a flexible membrane on the elongated body portion adjacent the spring member and wherein the step of actuating the movable member moves the spring member in the first direction to simultaneously cause stretching of the membrane positioned on the elongated body portion such that the membrane contacts the body tissue.

* * * * *